US012671002B2

(12) United States Patent
Embree et al.

(10) Patent No.: US 12,671,002 B2
(45) Date of Patent: Jun. 30, 2026

(54) COMMUNICATION SYSTEM FOR PATIENT SUPPORT APPARATUSES

(71) Applicant: Hill-Rom Services, Inc., Batesville, IN (US)

(72) Inventors: Stephen R. Embree, Chapel Hill, NC (US); Frederick C. Davidson, Apex, NC (US); Theophile R. Lerebours, Cary, NC (US); Phillip Maloney, Raleigh, NC (US); Bruno J. Filliat, Cary, NC (US); David M. Girardeau, Pittsboro, NC (US); Christian Saucier, Raleigh, NC (US); Kelly F. Walton, Cary, NC (US); Joshua P. Lingenfelser, Fuquay-Varina, NC (US); Benjamin E. Howell, Fuquay-Varina, NC (US); Bradley T. Smith, Raleigh, NC (US); Laura A. Hassey, Raleigh, NC (US); Stephen N. Moore, Apex, NC (US); Britten J. Pipher, Raleigh, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 252 days.

(21) Appl. No.: 18/367,027

(22) Filed: Sep. 12, 2023

(65) Prior Publication Data

US 2024/0047085 A1     Feb. 8, 2024

Related U.S. Application Data

(60) Continuation of application No. 16/434,544, filed on Jun. 7, 2019, now Pat. No. 11,791,055, which is a
(Continued)

(51) Int. Cl.
G16H 80/00 (2018.01)
G08B 25/12 (2006.01)
(Continued)

(52) U.S. Cl.
CPC ............. G16H 80/00 (2018.01); G08B 25/12 (2013.01); G16H 40/63 (2018.01); H04L 67/12 (2013.01); H04L 69/18 (2013.01)

(58) Field of Classification Search
CPC ........ G16H 80/00; G16H 40/63; G08B 25/12; H04L 67/12; H04L 69/18
See application file for complete search history.

(56) References Cited

U.S. PATENT DOCUMENTS 5,003,984 A     4/1991  Muraki et al.
5,228,449 A     7/1993  Christ et al.
(Continued)

FOREIGN PATENT DOCUMENTS

DE     10 2006 056 723     7/2007
EP         0 601 589     6/1994
(Continued)

OTHER PUBLICATIONS

Communication pursuant to Article 94(3) EFC mailed by the European Patent Office on Jun. 26, 2024, in European Patent Application No. 21195316.1 (8 pages).
(Continued)

*Primary Examiner* — Brian Wilson
(74) *Attorney, Agent, or Firm* — Barnes & Thornburg LLP

(57) ABSTRACT

According to the present disclosure, devices, systems, and methods for locating, tracking, and conducting communications between care devices and networks of care facilities through local communications hubs.

20 Claims, 17 Drawing Sheets

Related U.S. Application Data division of application No. 15/498,426, filed on Apr. 26, 2017, now Pat. No. 10,360,787.

(60) Provisional application No. 62/332,223, filed on May 5, 2016.

(51) Int. Cl.
    *G16H 40/63*       (2018.01)
    *H04L 67/12*       (2022.01)
    *H04L 69/18*       (2022.01)

(56) References Cited

U.S. PATENT DOCUMENTS

| | | | |
|---|---|---|---|
| 5,319,363 A | 6/1994 | Welch et al. |
| 5,394,882 A | 3/1995 | Mawhinney |
| 5,511,553 A | 4/1996 | Segalowitz |
| 5,544,661 A | 8/1996 | Davis et al. |
| 5,579,775 A | 12/1996 | Dempsey et al. |
| 5,628,324 A | 5/1997 | Sarbach |
| 5,678,562 A | 10/1997 | Sellers |
| 5,712,795 A | 1/1998 | Layman et al. |
| 5,713,856 A | 2/1998 | Eggers et al. |
| 5,719,761 A | 2/1998 | Gatti et al. |
| 5,724,025 A | 3/1998 | Tavori |
| 5,781,442 A | 7/1998 | Engleson et al. |
| 5,800,387 A | 9/1998 | Duffy et al. |
| 5,825,283 A | 10/1998 | Camhi |
| 5,836,910 A | 11/1998 | Duffy et al. |
| 5,862,803 A | 1/1999 | Besson et al. |
| 5,873,369 A | 2/1999 | Laniado et al. |
| 5,919,141 A | 7/1999 | Money et al. |
| 5,941,846 A | 8/1999 | Duffy et al. |
| 5,944,659 A | 8/1999 | Flach et al. |
| 5,957,854 A | 9/1999 | Beeson et al. |
| 5,990,866 A | 11/1999 | Yollin |
| 6,014,346 A | 1/2000 | Malone |
| 6,038,469 A | 3/2000 | Karlsson et al. |
| 6,044,283 A | 3/2000 | Fein et al. |
| 6,044,382 A | 3/2000 | Martino |
| 6,047,203 A | 4/2000 | Sackner et al. |
| 6,057,758 A | 5/2000 | Dempsey et al. |
| 6,074,345 A | 6/2000 | van Oostrom et al. |
| 6,080,106 A | 6/2000 | Lloyd et al. |
| 6,093,146 A | 7/2000 | Filangeri |
| 6,132,371 A | 10/2000 | Dempsey et al. |
| 6,147,618 A | 11/2000 | Halleck et al. |
| 6,150,951 A | 11/2000 | OleJniczak |
| 6,159,147 A | 12/2000 | Lichter et al. |
| 6,160,478 A | 12/2000 | Jacobsen et al. |
| 6,167,258 A | 12/2000 | Schmidt et al. |
| 6,171,264 B1 | 1/2001 | Bader |
| 6,186,962 B1 | 2/2001 | Lloyd et al. |
| 6,198,394 B1 | 3/2001 | Jacobsen et al. |
| 6,213,942 B1 | 4/2001 | Flach et al. |
| 6,270,457 B1 | 8/2001 | Bardy |
| 6,277,080 B1 | 8/2001 | Nissila et al. |
| 6,289,238 B1 | 9/2001 | Besson et al. |
| 6,304,774 B1 | 10/2001 | Gorman |
| 6,336,900 B1 | 1/2002 | Alleckson et al. |
| 6,336,903 B1 | 1/2002 | Bardy |
| 6,368,284 B1 | 4/2002 | Bardy |
| 6,398,727 B1 | 6/2002 | Bui et al. |
| 6,398,728 B1 | 6/2002 | Bardy |
| 6,402,691 B1 | 6/2002 | Peddicord et al. |
| 6,406,426 B1 | 6/2002 | Reuss et al. |
| 6,407,335 B1 | 6/2002 | Franklin-Lees et al. |
| 6,411,840 B1 | 6/2002 | Bardy |
| 6,416,471 B1 | 7/2002 | Kumar et al. |
| 6,437,692 B1 | 8/2002 | Petite et al. |
| 6,441,747 B1 | 8/2002 | Khair et al. |
| 6,443,890 B1 | 9/2002 | Schulze et al. |
| 6,450,953 B1 | 9/2002 | Place et al. |
| 6,475,153 B1 | 11/2002 | Khair et al. |
| 6,493,747 B2 | 12/2002 | Simmon et al. |
| 6,494,829 B1 | 12/2002 | New, Jr. et al. |
| 6,496,705 B1 | 12/2002 | Ng et al. |
| 6,497,656 B1 | 12/2002 | Evans et al. |
| 6,517,497 B2 | 2/2003 | Rymut et al. |
| 6,533,729 B1 | 3/2003 | Khair et al. |
| 6,540,686 B2 | 4/2003 | Heikkilaet et al. |
| 6,544,173 B2 | 4/2003 | West et al. |
| 6,544,174 B2 | 4/2003 | West et al. |
| 6,551,252 B2 | 4/2003 | Sackner et al. |
| 6,559,620 B2 | 5/2003 | Zhou et al. |
| 6,569,094 B2 | 5/2003 | Suzuki et al. |
| 6,575,902 B1 | 6/2003 | Burton |
| 6,577,893 B1 | 6/2003 | Besson et al. |
| 6,579,231 B1 | 6/2003 | Phipps |
| 6,589,170 B1 | 7/2003 | Flach et al. |
| 6,593,528 B2 | 7/2003 | Franklin-Lees et al. |
| 6,594,511 B2 | 7/2003 | Stone et al. |
| 6,595,929 B2 | 7/2003 | Stivoric et al. |
| 6,602,191 B2 | 8/2003 | Quy |
| 6,603,401 B1 | 8/2003 | Ueyama |
| 6,605,038 B1 | 8/2003 | Teller et al. |
| 6,611,705 B2 | 8/2003 | Hopman et al. |
| 6,612,984 B1 | 9/2003 | Kerr, II |
| 6,616,606 B1 | 9/2003 | Petersen et al. |
| 6,640,246 B1 | 10/2003 | Gary, Jr. et al. |
| 6,659,947 B1 | 12/2003 | Carter et al. |
| 6,669,630 B1 | 12/2003 | Joliat et al. |
| 6,671,563 B1 | 12/2003 | Engelson et al. |
| 6,693,514 B2 | 2/2004 | Perea, Jr. et al. |
| 6,694,180 B1 | 2/2004 | Boesen |
| 6,723,046 B2 | 4/2004 | Lichtenstein et al. |
| 6,731,989 B2 | 5/2004 | Engleson et al. |
| 6,736,759 B1 | 5/2004 | Stubbs et al. |
| 6,740,033 B1 | 5/2004 | Olejniczak et al. |
| 6,748,250 B1 | 6/2004 | Berman et al. |
| 6,749,566 B2 | 6/2004 | Russ |
| 6,758,812 B2 | 7/2004 | Lang |
| 6,773,396 B2 | 8/2004 | Flach et al. |
| 6,817,979 B2 | 11/2004 | Nihtila |
| 6,819,247 B2 | 11/2004 | Birnbach et al. |
| 6,823,036 B1 | 11/2004 | Chen |
| 6,840,904 B2 | 1/2005 | Goldberg |
| 6,870,466 B2 | 3/2005 | Rust et al. |
| 6,871,211 B2 | 3/2005 | Labounty et al. |
| 6,875,174 B2 | 4/2005 | Braun et al. |
| 6,893,396 B2 | 5/2005 | Schulze et al. |
| 6,897,788 B2 | 5/2005 | Khair et al. |
| 6,915,170 B2 | 7/2005 | Engleson et al. |
| 6,937,150 B2 | 8/2005 | Medema et al. |
| 6,942,616 B2 | 9/2005 | Kerr, II |
| 6,984,297 B2 | 1/2006 | Nisch et al. |
| 6,987,965 B2 | 1/2006 | Ng et al. |
| 6,988,989 B2 | 1/2006 | Weiner et al. |
| 7,002,468 B2 | 2/2006 | Eveland et al. |
| 7,004,907 B2 | 2/2006 | Banet et al. |
| 7,010,337 B2 | 3/2006 | Furnary et al. |
| 7,020,508 B2 | 3/2006 | Stivoric et al. |
| 7,029,455 B2 | 4/2006 | Flaherty |
| 7,053,767 B2 | 5/2006 | Petite et al. |
| 7,053,831 B2 | 5/2006 | Dempsey et al. |
| 7,088,233 B2 | 8/2006 | Menard |
| 7,099,895 B2 | 8/2006 | Dempsey |
| 7,103,407 B2 | 9/2006 | Hjelt et al. |
| 7,103,511 B2 | 9/2006 | Petite |
| 7,104,955 B2 | 9/2006 | Bardy |
| 7,107,106 B2 | 9/2006 | Engleson et al. |
| 7,117,041 B2 | 10/2006 | Engleson et al. |
| 7,123,149 B2 | 10/2006 | Nowak et al. |
| 7,127,261 B2 | 10/2006 | Van Erlach |
| 7,129,836 B2 | 10/2006 | Lawson et al. |
| 7,130,396 B2 | 10/2006 | Rogers et al. |
| 7,138,902 B2 | 11/2006 | Menard |
| 7,153,262 B2 | 12/2006 | Stivoric et al. |
| 7,153,263 B2 | 12/2006 | Carter et al. |
| 7,154,398 B2 | 12/2006 | Chen et al. |
| 7,156,807 B2 | 1/2007 | Carter et al. |
| 7,171,166 B2 | 1/2007 | Ng et al. |
| 7,197,357 B2 | 3/2007 | Istvan et al. |
| 7,197,492 B2 | 3/2007 | Sullivan |

(56)          References Cited

U.S. PATENT DOCUMENTS

| | | |
|---|---|---|
| 7,215,991 B2 | 5/2007 | Besson et al. |
| 7,222,054 B2 | 5/2007 | Geva |
| 7,231,258 B2 | 6/2007 | Moore et al. |
| 7,256,708 B2 | 8/2007 | Rosenfeld et al. |
| 7,272,428 B2 | 9/2007 | Hopman et al. |
| 7,277,758 B2 | 10/2007 | DiLorenzo |
| 7,283,423 B2 | 10/2007 | Holm et al. |
| 7,292,135 B2 | 11/2007 | Bixler et al. |
| 7,292,139 B2 | 11/2007 | Mazar et al. |
| 7,294,105 B1 | 11/2007 | Islam |
| 7,301,451 B2 | 11/2007 | Hastings |
| 7,304,580 B2 | 12/2007 | Sullivan et al. |
| 7,324,824 B2 | 1/2008 | Smith et al. |
| 7,336,563 B2 | 2/2008 | Holm |
| 7,352,652 B2 | 4/2008 | Holm et al. |
| 7,362,656 B2 | 4/2008 | Holm |
| 7,384,110 B2 | 6/2008 | Hoshiyama et al. |
| 7,399,205 B2 | 7/2008 | McNeely et al. |
| 7,468,661 B2 | 12/2008 | Petite et al. |
| 7,598,853 B2 | 10/2009 | Becker et al. |
| 7,697,492 B2 | 4/2010 | Petite |
| 7,737,827 B2 | 6/2010 | Perkins et al. |
| 8,001,235 B2 | 8/2011 | Russ et al. |
| 8,082,160 B2 | 12/2011 | Collins, Jr. et al. |
| 8,102,254 B2 | 1/2012 | Becker et al. |
| 8,272,892 B2 | 9/2012 | McNeely et al. |
| 8,319,633 B2 | 11/2012 | Becker et al. |
| 8,674,826 B2 | 3/2014 | Becker et al. |
| 8,727,804 B2 | 5/2014 | McNeely et al. |
| 8,756,078 B2 | 6/2014 | Collins, Jr. et al. |
| 9,142,923 B2 | 9/2015 | McNeely et al. |
| 10,360,787 B2 | 7/2019 | Embree et al. |
| 10,709,624 B2* | 7/2020 | Bhimavarapu ........ A61G 7/018 |
| 11,791,055 B2 | 10/2023 | Embree et al. |
| 2001/0034475 A1 | 10/2001 | Flach et al. |
| 2002/0165731 A1 | 11/2002 | Dempsey |
| 2002/0198986 A1 | 12/2002 | Dempsey |
| 2003/0069806 A1* | 4/2003 | Konomi ............ G06Q 30/0601 |
| | | 705/26.1 |
| 2003/0141981 A1 | 7/2003 | Bui et al. |
| 2004/0072475 A1 | 4/2004 | Istvan |
| 2004/0073127 A1 | 4/2004 | Istvan et al. |
| 2004/0121767 A1 | 6/2004 | Simpson et al. |
| 2004/0127802 A1 | 7/2004 | Istvan et al. |
| 2004/0147818 A1 | 7/2004 | Levy et al. |
| 2004/0167465 A1 | 8/2004 | Mihai et al. |
| 2004/0176667 A1 | 9/2004 | Mihai et al. |
| 2004/0186358 A1 | 9/2004 | Chernow et al. |
| 2004/0259494 A1 | 12/2004 | Mazar |
| 2005/0035862 A1 | 2/2005 | Wildman et al. |
| 2005/0038326 A1 | 2/2005 | Mathur |
| 2005/0065817 A1 | 3/2005 | Mihai et al. |
| 2005/0102167 A1 | 5/2005 | Kapoor |
| 2005/0119866 A1 | 6/2005 | Zaleski |
| 2005/0140508 A1 | 6/2005 | Tessier et al. |
| 2005/0144042 A1 | 6/2005 | Joffe et al. |
| 2005/0148303 A1 | 7/2005 | Dempsey |
| 2005/0177052 A1 | 8/2005 | Istvan et al. |
| 2005/0197545 A1 | 9/2005 | Hoggle |
| 2005/0206518 A1 | 9/2005 | Welch et al. |
| 2005/0246416 A1 | 11/2005 | Blomquist |
| 2005/0251002 A1 | 11/2005 | Istvan et al. |
| 2005/0251003 A1 | 11/2005 | Istvan et al. |
| 2005/0251004 A1 | 11/2005 | Istvan et al. |
| 2006/0002340 A1 | 1/2006 | Criss et al. |
| 2006/0030759 A1 | 2/2006 | Weiner et al. |
| 2006/0049936 A1 | 3/2006 | Collins et al. |
| 2006/0077759 A1 | 4/2006 | Holm |
| 2006/0089539 A1 | 4/2006 | Miodownik et al. |
| 2006/0095234 A1 | 5/2006 | Brignone et al. |
| 2006/0106649 A1 | 5/2006 | Eggers et al. |
| 2006/0122867 A1 | 6/2006 | Eggers et al. |
| 2006/0136271 A1 | 6/2006 | Eggers et al. |
| 2006/0143051 A1 | 6/2006 | Eggers et al. |
| 2006/0190302 A1 | 8/2006 | Eggers et al. |

| | | |
|---|---|---|
| 2006/0214786 A1 | 9/2006 | Bixler et al. |
| 2006/0217987 A1* | 9/2006 | Sowada ........... H04N 21/42204 |
| | | 348/E5.122 |
| 2006/0220839 A1 | 10/2006 | Fifolt et al. |
| 2006/0238350 A1 | 10/2006 | Tessier |
| 2006/0239195 A1 | 10/2006 | Camins et al. |
| 2006/0242293 A1 | 10/2006 | Russ |
| 2006/0248221 A1 | 11/2006 | Hottel et al. |
| 2006/0253281 A1 | 11/2006 | Letzt et al. |
| 2006/0258926 A1 | 11/2006 | Ali et al. |
| 2006/0267740 A1 | 11/2006 | Bixler et al. |
| 2006/0277202 A1 | 12/2006 | Dempsey |
| 2006/0279427 A1 | 12/2006 | Becker et al. |
| 2006/0288095 A1 | 12/2006 | Torok et al. |
| 2007/0013511 A1 | 1/2007 | Weiner et al. |
| 2007/0060976 A1 | 3/2007 | Denzene et al. |
| 2007/0069887 A1 | 3/2007 | Welch et al. |
| 2007/0112602 A1 | 5/2007 | Bellon et al. |
| 2007/0120689 A1 | 5/2007 | Zerhusen |
| 2007/0123955 A1 | 5/2007 | Verhoef et al. |
| 2007/0135866 A1 | 6/2007 | Baker et al. |
| 2007/0136102 A1 | 6/2007 | Rodgers |
| 2007/0142716 A1 | 6/2007 | Biondi |
| 2007/0156456 A1 | 7/2007 | McGillin et al. |
| 2007/0156707 A1 | 7/2007 | Fuchs et al. |
| 2007/0180140 A1 | 8/2007 | Welch et al. |
| 2007/0208235 A1 | 9/2007 | Besson et al. |
| 2007/0210917 A1 | 9/2007 | Collins et al. |
| 2007/0214013 A1 | 9/2007 | Silverman |
| 2007/0214357 A1 | 9/2007 | Baldus |
| 2007/0229249 A1 | 10/2007 | McNeal et al. |
| 2007/0233199 A1 | 10/2007 | Moore et al. |
| 2007/0251835 A1 | 11/2007 | Mehta et al. |
| 2007/0255111 A1 | 11/2007 | Baldus et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0279211 A1 | 12/2007 | Fenske et al. |
| 2007/0288263 A1 | 12/2007 | Rodgers |
| 2008/0009694 A1 | 1/2008 | Hopman et al. |
| 2008/0018435 A1 | 1/2008 | Brown |
| 2008/0049555 A1 | 2/2008 | Holm et al. |
| 2008/0114689 A1 | 5/2008 | Psynik et al. |
| 2008/0120784 A1 | 5/2008 | Warner et al. |
| 2008/0122616 A1 | 5/2008 | Warner et al. |
| 2008/0126122 A1 | 5/2008 | Warner et al. |
| 2008/0126132 A1 | 5/2008 | Warner et al. |
| 2008/0147442 A1 | 6/2008 | Warner et al. |
| 2008/0164998 A1 | 7/2008 | Scherpbier et al. |
| 2009/0112630 A1 | 4/2009 | Collins, Jr. et al. |
| 2009/0204977 A1 | 8/2009 | Tavares |
| 2010/0001838 A1 | 1/2010 | Miodownik et al. |
| 2011/0134339 A1* | 6/2011 | Butler .............. H04N 21/42222 |
| | | 348/734 |
| 2011/0250842 A1* | 10/2011 | Stafford ................ H04W 24/02 |
| | | 455/41.2 |
| 2012/0164877 A1 | 6/2012 | Wallace |
| 2012/0330109 A1 | 12/2012 | Tran |
| 2013/0300548 A1* | 11/2013 | Robinson ............... G16H 40/20 |
| | | 340/286.07 |
| 2014/0282746 A1 | 9/2014 | Lin |
| 2014/0297310 A1 | 10/2014 | Collins, Jr. |
| 2014/0297327 A1* | 10/2014 | Heil ...................... G16H 40/40 |
| | | 700/282 |
| 2015/0015417 A1 | 1/2015 | Libbus et al. |
| 2015/0081335 A1* | 3/2015 | Dixon .................... H04W 4/33 |
| | | 705/2 |
| 2015/0082542 A1 | 3/2015 | Hayes |
| 2015/0243162 A1 | 8/2015 | Daum |
| 2016/0029889 A1 | 2/2016 | Baker et al. |
| 2016/0038361 A1 | 2/2016 | Bhimavarapu et al. |
| 2016/0296143 A1* | 10/2016 | Hayes .................. A61B 5/1115 |
| 2017/0099198 A1 | 4/2017 | Bhimavarapu |

(56) References Cited

U.S. PATENT DOCUMENTS

| | | |
|---|---|---|
| 2017/0323555 A1 | 11/2017 | Embree et al. |
| 2019/0287385 A1 | 9/2019 | Embree et al. |

FOREIGN PATENT DOCUMENTS

| | | |
|---|---|---|
| EP | 1 480 388 | 11/2004 |
| EP | 1 734 458 | 12/2006 |
| EP | 2 093 980 | 8/2009 |
| WO | WO 2003/102851 | 12/2003 |
| WO | WO 2004/028344 | 4/2004 |
| WO | WO 2005/114524 | 12/2005 |
| WO | WO 2007/063157 | 6/2007 |
| WO | WO 2008/004205 | 1/2008 |
| WO | WO 2008/033970 | 3/2008 |
| WO | WO 2008/067176 | 6/2008 |
| WO | WO 2013/0165692 | 11/2013 |

OTHER PUBLICATIONS

Communication pursuant to Article 94(3) EPC from the European Patent Office regarding European Patent Application No. 17169806.1 dated Mar. 27, 2019; 11 pages.
Communication pursuant to Rule 62 EPC for European Application No. 17169806.1-1853; dated Oct. 10, 2017; 12 pages.

* cited by examiner

TO NETWORK          115

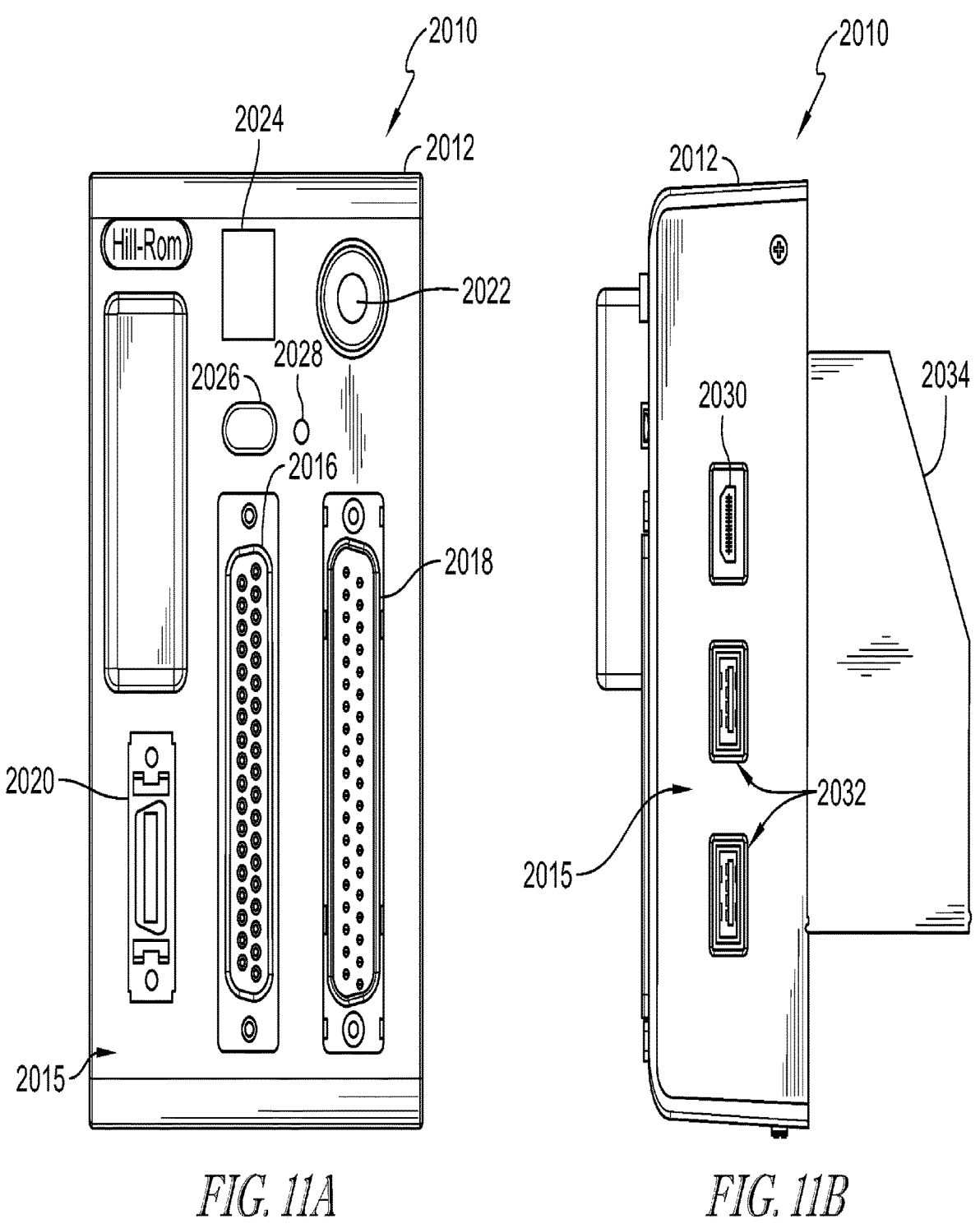
*FIG. 11A*          *FIG. 11B*

COMMUNICATION SYSTEM FOR PATIENT SUPPORT APPARATUSES

CROSS-REFERENCE TO RELATED APPLICATION

This application is a continuation of U.S. application Ser. No. 16/434,544, filed Jun. 7, 2019, now U.S. Pat. No. 11,791,055, which is a divisional application of U.S. application Ser. No. 15/498,426, filed on Apr. 26, 2017, now U.S. Pat. No. 10,360,787, which claims the benefit, under 35 U.S.C. § 119(e), of U.S. Provisional Application No. 62/332,223, filed on May 5, 2016, the contents of each of which are hereby incorporated by reference in their entirety.

BACKGROUND

The present disclosure relates to devices, systems, and methods for managing communications within care facilities. More specifically, devices, systems, and methods for managing communications of patient devices and networks of care facilities.

Care facilities, such as hospitals, use many types of communications in managing patients, staff, and equipment. The increasingly interconnected environments within care facilities present potential for miscommunications but also provide opportunity for increased coordination between systems of the care facility. Managing communications appropriately can reduce miscommunication and promote coordination.

SUMMARY

The present application discloses one or more of the features recited in the appended claims and/or the following features which, alone or in any combination, may comprise patentable subject matter:

According to an aspect of the present disclosure, a communications system may include devices, systems, and methods for discriminating communications within a care facility, may conduct location monitoring and tracking, and may conduct location-based operations of various devices and systems.

According to another aspect of the present disclosure, a patient care communications system of a care facility may include a patient bed having a bed ID associated therewith. A bed communications device may be attached to the patient bed and may be configured to send and receive bed communications signals. A local communications device may be associated with a room of the care facility. The local communications device may be configured to communicate first signals that may have a first wavelength and that may be configured to communicate second signals that may have a second wavelength that may be different than the first wavelength. The local communications device may be configured to receive at least one bed communications signal that may indicate the bed ID of the patient bed and to send a confirmation signal indicating the bed ID.

In some embodiments, the confirmation signal may include the first signals. The confirmation signal may include an infrared signal, for example. In some embodiments, the second signals may include one of a Bluetooth signal and a Wi-Fi signal.

In some embodiments, the bed communications device may be configured to receive the confirmation signal that may indicate the bed ID from the local communications device and to establish an ad-hoc personal area network with the local communications device in response to a determination that the bed ID indicated by the confirmation signal corresponds to the patient bed.

In some embodiments, the ad-hoc personal area network may be a piconet. In some embodiments, the local communication device may be configured to communicate with a network of the care facility.

In some embodiments, the ad-hoc network may provide a communications link for communication between the bed communications device and the network of the care facility.

In some embodiments, the bed communication device may prevent formation of an ad-hoc network with the local communications device if no confirmation signal is received.

According to another aspect of the present disclosure patient care communications system of a care facility may include a patient bed having a bed ID associated therewith and a bed communications device that may be attached to the patient bed. The bed communications device may be configured to communicate at least one first signal that may have a first wavelength and may be configured to communicate at least one second signal that may have a second wavelength different than the first wavelength. A local communications device may be associated with a room of the care facility. The local communications device may be configured for communication with the bed communications device. In response to receiving at least one confirmation signal indicating the bed ID, the bed communications device may form an ad-hoc network with the local communications device.

In some embodiments, the at least one confirmation signal may include the at least one first signal. The at least one first signal may include an infrared signal.

In some embodiments, the bed communications device may communicate the bed ID to the local communications device through a bed communications signal that may comprise the at least one second signal.

In some embodiments, the ad-hoc network may be a piconet that may include Bluetooth signals.

In some embodiments, the local communication device may be configured to communicate with a network of the care facility.

In some embodiments, the ad-hoc network may provide a communications link between the bed communications device and the network of the care facility.

In some embodiments, the patient care communications system may include a second patient bed that may have a second bed ID and a second bed communications device that may be attached to the second patient bed. In response to receiving at least one confirmation signal indicating the second bed ID, the second bed communications device may form an ad-hoc network with the local communications device.

In some embodiments, the local communications device may send the at least one confirmation signal indicating the second bed ID in response to receiving the second bed ID from the second bed communications device.

According to another aspect of the present disclosure, a patient care communications system of a care facility may include a patient bed, a bed communications device that may be attached to the patient bed, and a local communications device that may be associated with a room of the care facility. The local communications device may be configured to communicate at least one infrared signal that may indicate an ID code. The bed communications device may receive the at least one infrared signal and may form an ad-hoc network with the local communications device by sending a confirmation signal indicating the ID code.

In some embodiments, the confirmation signal may be one of Bluetooth and Wi-Fi.

According to another aspect of the present disclosure, a patient care communications system of a care facility may include a patient bed and a bed communications device that may be attached to the patient bed. The bed communications device may be configured to communicate at least one infrared signal that may indicate an ID code. A local communications device may be associated with a room of the care facility. The local communications device may receive the at least one infrared signal and may form an ad-hoc network with the bed communications device by sending a confirmation signal indicating the ID code.

In some embodiments, the confirmation signal may be one of Bluetooth and Wi-Fi.

According to another aspect of the present disclosure, a method of establishing local communications between a patient support device and a local communications device may include sending a first signal from a first device that may indicate ID information, sending a second signal from a second device that may indicate ID information, determining whether the ID information of the first signal corresponds to the ID information of the second signal, and in response to a determination of correspondence, establishing an ad-hoc network between the first and second devices.

In some embodiments, the ad-hoc network may be a piconet that may include a Bluetooth transmission.

According to another aspect of the present disclosure, a patient care communications system of a care facility may include a patient bed, a bed communications device that may be attached to the patient bed, and a local communications device that may be associated with a room of the care facility and that may be configured for communication with the bed communications device. At least one of the local communications device and the bed communications device may transmit at least one ID signal indicating an ID code and may form an ad-hoc network with the other of the local communications device and the bed communications device upon receiving a confirmation signal indicating the ID code.

In some embodiments, one of the ID signal and the confirmation signal may include a wavelength that is insufficient to communicate through walls of the care facility and the other of the ID signal and the confirmation signal may include a wavelength that is sufficient to communicate through walls of the care facility.

In some embodiments, one of the ID signal and the confirmation signal may be an infrared signal and the other of the ID signal and the confirmation signal may be at least one of a Bluetooth signal and a Wi-Fi signal.

According to another aspect of the present disclosure, a discriminating patient care communications system for communication with a network of a care facility may include a plurality of communication hubs that each may include circuitry that may be configured to send and receive communication signals. A signal meter may be configured to measure the strength of signals received. A number of the plurality of communication hubs may be arranged in communication with each other. At least one network hub of the plurality of communication hubs may be arranged in communication with the network of the care facility. A patient bed may include communication circuitry that may be configured to send signals that may indicate bed information to at least one of the plurality of communication hubs.

The system may further include at least one patient care device for attending a patient that may be assigned to the patent bed. The at least one patient care device may include communication circuitry that may be configured to send signals that may indicate care device information to at least one of the plurality of communication hubs. The plurality of communication hubs may be configured to determine a preferred hub of the plurality of communication hubs for communication with the at least one patient care device based on the greatest signal strength as measured by the signal meter and may be configured to selectively operate the preferred hub to receive the signals that may indicate care device information from the at least one patient care device. The plurality of communication hubs may also be configured to communicate an indication of the care device information to the network through the at least one network hub and to selectively operate the communication hubs, other than the preferred hub, to disregard the signals indicating care device information.

According to another aspect of the present disclosure, a patient care communications system of a care facility that may have a facility communications system may include a patient-care device that may include at least one audio speaker, a patient-care communications device that may be attached to the patient-care device, and a local communications device that may be associated with a room of the care facility and that may be configured for communication with the facility communications system and the patient-care communications device to communicate information therebetween. In some embodiments, one of the local communications device and the patient-care communications device may form an ad-hoc network with the other of the local communications device and the patient-care communications device. In some embodiments, the local communication device may be configured to prioritize audio signals communicated from the facility communications system.

In some embodiments, the audio speaker may be configured to provide audio for one or more entertainment devices associated with the room of the care facility. In some embodiments, prioritizing audio signals may include stopping audio play from the speaker provided from the one or more entertainment devices in favor of audio from the facility communications system.

According to another aspect of the present disclosure, a patient care communications system for communication with a network of a care facility may include a plurality of communications hubs that may include at least one communications hub that may be arranged within a room of the care facility that may be equipped with a preferred nurse call communications system. At least two communications hubs may be arranged within a room of the care facility equipped with a non-preferred nurse call communications system. A number of patient care devices may each include communication circuitry that may be configured to communicate signals to at least one of the plurality of communication hubs. In some embodiments, a first of the at least two communications hubs may be arranged within a room of the care facility that may be equipped with a non-preferred nurse call communications system and that may be in communication with the non-preferred nurse call communications system. In some embodiments, a second of the at least two communications hubs may be in communication with the network of the care facility.

In some embodiments, the first of the at least two communications hubs may communicate with the network through the second of the at least two communications hubs. In some embodiments, the second of the at least two communications hubs may communicate with the non-preferred nurse call communications system through the first of the at least two communications hubs.

According to another aspect of the present disclosure, a patient care communications system for communication with a network of a care facility may include a plurality of communications hubs that may include at least two communications hubs that may be arranged within a room of the care facility that may be equipped with a non-preferred nurse call communications system. A number of patient care devices may each include communication circuitry that may be configured to communicate signals to at least one of the plurality of communication hubs. A first of the at least two communications hubs may be arranged within a room of the care facility that may be equipped with a non-preferred nurse call communications system and may be in communication with the non-preferred nurse call communications system. A second of the at least two communications hubs may be in communication with the network of the care facility.

In some embodiments, the first of the at least two communications hubs may communicate with the network through the second of the at least two communications hubs. In some embodiments, the second of the at least two communications hubs may communicate with the non-preferred nurse call communications system through the first of the at least two communications hubs.

Additional features alone or in combination with any other feature(s), including those listed above and those listed in the claims and those described in detail below, may comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 11A is front elevation view of another illustrative embodiment of a communications hub of the patient care communications system of FIGS. 4 and 6-10;

FIG. 11B is a side elevation view of the communications hub of FIG. 11A;

DETAILED DESCRIPTION OF THE DRAWINGS

Information sharing within care facilities, such as hospitals, is increasingly important to patient care. Care facilities increasingly use wireless communications to facilitate information sharing. Within a given area of a care facility, multiple communication signals may exist such that the potential arises for miscommunication between the sources and intended receivers of communication signals.

Wireless communication signals often have different effective ranges, whether long- or short-range, that can be configured to decrease the potential for miscommunication between sources and receivers. For example, a short-range communication source signal can reliably inhibit mistaken communications with a receiver that is outside the effective broadcast range of that source signal. However, care facilities are often arranged such that signal sources and receivers are separated by walls, but not by large distances. Thus, range-limited miscommunication control can provide incomplete protection against miscommunication. Moreover, such range-limited miscommunication control presents practical difficulties in installation, calibration, verification, and modification, among others. The present disclosure includes devices, systems, and methods for reliably establishing wireless communications such that communications within the intended area are authorized (acknowledged) and communications outside the intended area are denied (disregarded).

Figure 1:
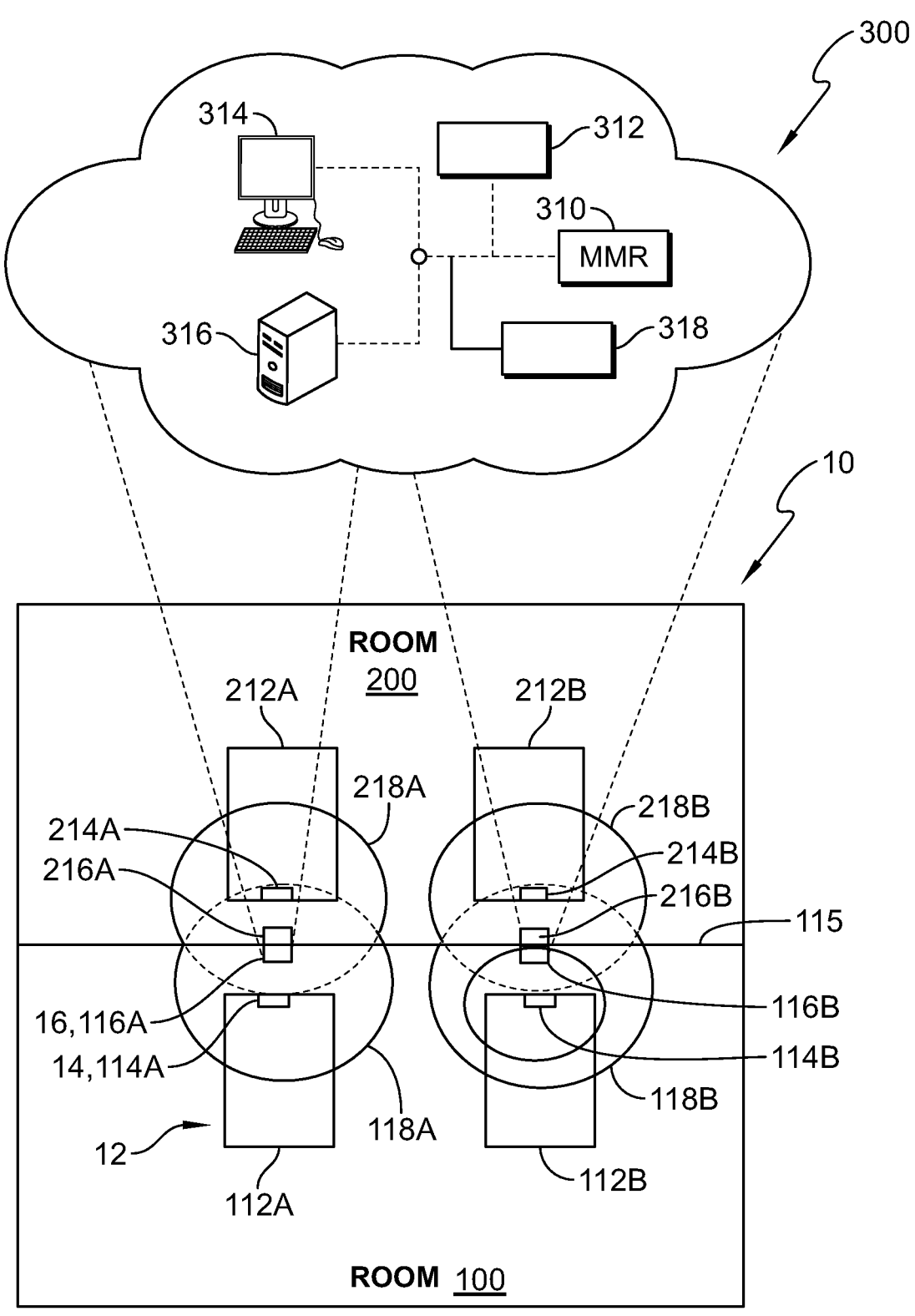
FIG. 1 is a diagrammatic plan view of patient rooms of a care facility showing an illustrative embodiment of a patient care communications system providing communications between patient beds each having a bed communications device and a network of the care facility through local communications devices upon establishing ad-hoc networks.

An illustrative embodiment of a patient care communications system 10 of a care facility is shown in FIG. 1. The patient care communications system 10 illustratively includes a patient support device illustratively embodied as a patient bed 12, a bed communications device 14 attached to the bed 12, and a local communications device 16 in communication with a network 300 of the care facility. As discussed below, the bed communications device 14 and the local communications device 16 can communicate to form an ad-hoc network through which the bed communications device 14 can communicate information with the network 300.

An exemplary bed 12 is embodied as bed 112A in communication with exemplary local communications device 116A, each located within a room 100. The room 100 illustratively shares a wall 115 with another room 200. The room 200 illustratively includes another exemplary bed 12 embodied as bed 212A that is in communication with another exemplary local communications device 216A. As illustratively shown in FIG. 1, the local communications device 216A is within the broadcast range 118A of the bed communications device 114A despite being located within different rooms 100, 200 and separated by the wall 115. A potential for miscommunication exists between the beds 112A, 212A and their respective local communications devices 116A, 216A due to their close proximity and despite separation by the wall 115.

However, in the illustrative embodiment, ad-hoc networks are formed between the beds 12 and their respective local communications devices 16 only upon successful determination of correspondence using infrared signals. Because infrared signals are generally ineffective to communicate through walls, requiring correspondence through infrared signals before establishing ad-hoc networks can assist in distinguishing between specific signal sources and receivers.

In the illustrative embodiment, the local communications device 116A is associated with room 100. The local communications device 116A is illustratively mounted to the wall within the room 100 near to the location at which the bed 112A is positioned and within the effective range 118A of the bed communications device 114A. The local communications device 116A illustratively receives a unique bed identification code (bed $ID_{112A}$) from the bed 112A.

In the illustrative embodiment, the bed communications device 14 illustratively communicates a first signal (embodied to include a Bluetooth signal) indicating the bed $ID_{12}$. The local communications device 16 illustratively receives the first signal and communicates a second signal as a confirmation signal (embodied to include an infrared signal) indicating the bed $ID_{12}$ according to the received first signal. The bed 12 illustratively receives the confirmation signal and determines whether the first and second signals include corresponding bed IDs. The bed 12 can thus confirm correspondence between the bed IDs of the first signal and the correspondence signal to identify whether the local communications device 16 is within the same room as the bed 12. Upon determination of successful correspondence, the bed 12 forms an ad-hoc network with the local communications device 16, illustratively using Bluetooth low energy communications. In some embodiments, the ad-hoc network may include any suitable signal type and/or protocol.

With reference to the specific exemplary components in FIG. 1, the exemplary bed 112A illustratively communicates and confirms correspondence with the exemplary local communications device 116A to form an ad-hoc network therewith. The exemplary bed communications device 114A illustratively communicates a first signal (embodied to include a Bluetooth signal) indicating the bed $ID_{112A}$. The local communications device 116A illustratively receives the first signal and communicates a second signal as a confirmation signal (embodied to include an infrared signal) indicating the bed $ID_{112A}$ as indicated by the received first signal. The bed communication device 114A illustratively receives the confirmation signal and determines correspondence of the received bed $ID_{112A}$. The bed 112A can thus confirm correspondence between the bed IDs indicated by the first signal and the correspondence signal to identify whether the local communications device 116A is within the same room as the bed 112A. Upon determination of successful correspondence, the bed communications device 114A forms an ad-hoc network with the local communications device 116A, illustratively using Bluetooth low energy communications.

In comparison, the local communications device 216A can receive the first signal indicating the bed ID 112A from the bed 112A, but its infrared confirmation signal cannot effectively communicate correspondence through the wall 115 to confirm correspondence to the bed 112A. The local communications device 216A is illustratively positioned within the broadcast range 118A such that it can receive the first signal indicating the bed $ID_{112A}$ from the bed 112A. The local communications device 216A communicates a second signal as a confirmation signal (embodied as an infrared signal) indicating the bed $ID_{112A}$. However, because the confirmation signal is an infrared signal, it cannot effectively communicate through the wall 115 and thus bed 112A does not effectively receive the confirmation signal from the local communications device 216A. Moreover, the bed 212A is illustratively within range of the confirmation signal, but has its own unique bed $ID_{212A}$ and thus does not form an ad-hoc network with the local communications device 216A based on a non-corresponding bed $ID_{112A}$. As suggested in FIG. 1, when local communications device 216A receives (via Bluetooth) and confirms (via infrared) the bed $ID_{212A}$, the bed 212A illustratively forms an ad-hoc network with local communications device 216A.

Figure 2:
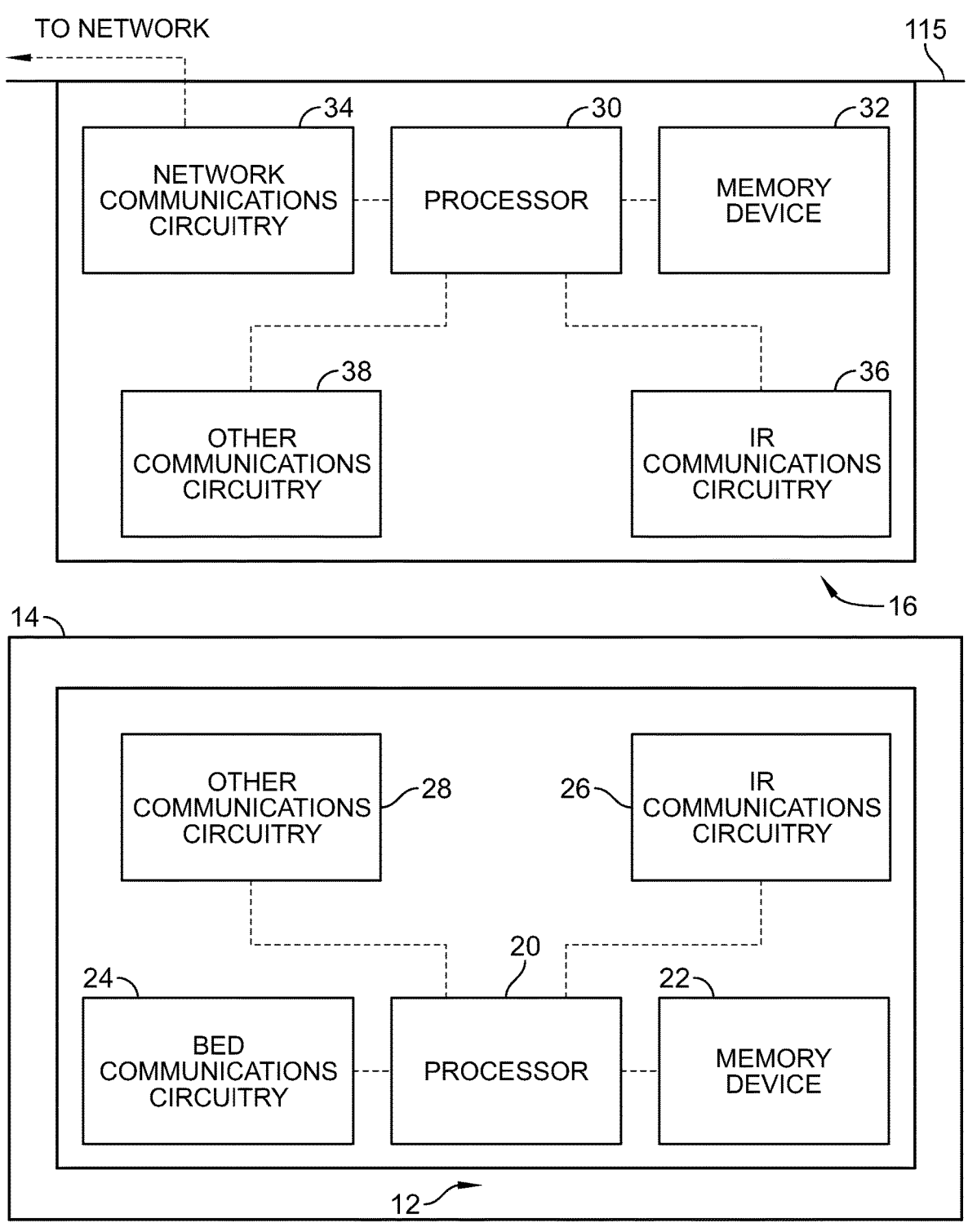
FIG. 2 is an diagrammatic view of one of the local communications devices in communication with one of the bed communications devices of FIG. 1.

In the illustrative embodiment as shown in FIG. 2, the bed communications device 14 illustratively includes at least one processor 20, at least one memory device 22 configured to store instructions for execution by the processor and communication circuitry 24 configured to receive and transmit communication signals with other bed systems, for example, a bed controller. The bed communications device 14 illustratively includes infrared (IR) communications circuitry 26 and other communications circuitry 28 configured to communicate with the local communications device 16.

As shown in FIG. 2, the local communications device 16 includes at least one processor 30, at least one memory device 32 configured to store instructions for execution by the processor 30, and network communications circuitry 34 configured to exchange (receive and transmit) communication signals with network 300. The local communications device 16 illustratively includes infrared (IR) communications circuitry 36 and other communications circuitry 38 configured to communicate with the bed communications device 14.

Figure 3:
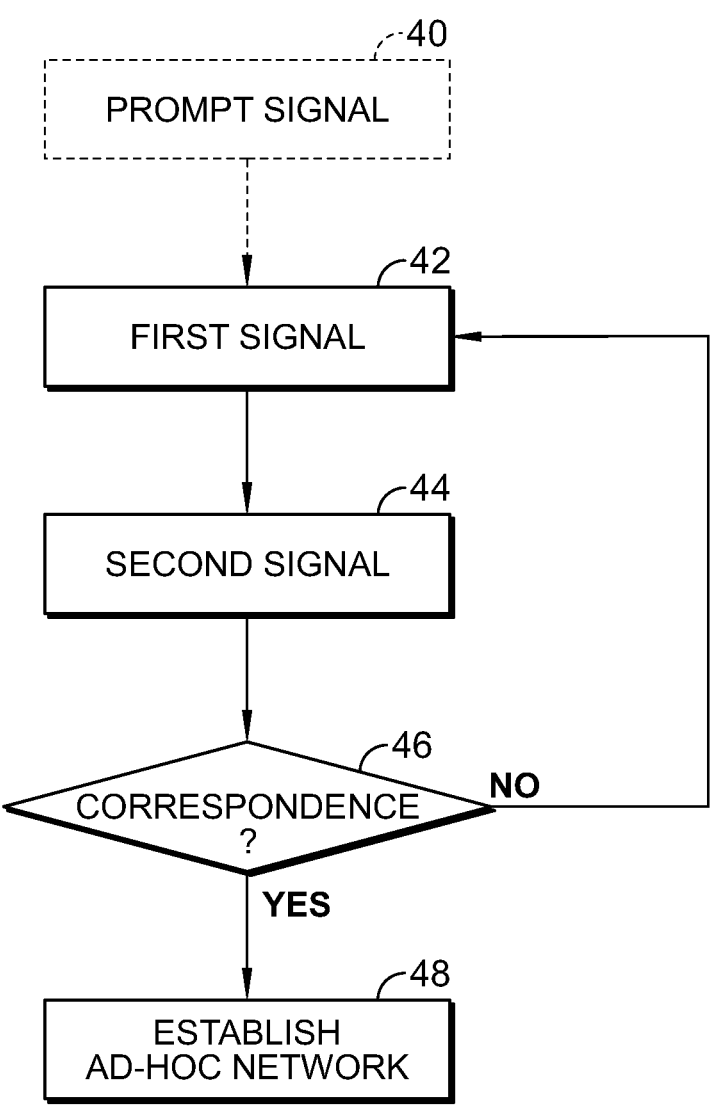
FIG. 3 is a process flow diagram of an illustrative operation of the establishing an ad-hoc network.

As shown in FIG. 3, a process flow diagram illustratively includes steps 40-48. The process steps 40-48 are described in terms of the illustrative embodiment of the patient care communications system 10, discussed above, but its description can apply to any of the arrangements and/or embodiments disclosed, whether expressly or implicitly, herein.

In step 42, a first signal is communicated indicating identifying information. The first signal is illustrative transmitted from a first device (embodied as the bed communications device 14) to a second device (embodied as the local communications device 16). The first signal is illustratively embodied as a Bluetooth signal indicating the bed ID. In step 42 of the illustrative process flow diagram, the first signal is illustratively transmitted at regular intervals. Optionally, the process may include step 40 in which the second device first sends a prompt signal to the first device to prompt sending of the first signal. After sending the first signal in step 42, the process proceeds to step 44.

In step 44, the second signal is transmitted indicating the identifying information according to the first signal. The second device illustratively transmits a second signal as a confirmation signal indicating the bed ID according to the first signal. In the illustrative embodiment, the confirmation signal is embodied as an IR signal indicating the bed ID according to the first signal. The process proceeds to step 46.

In step 46, correspondence is determined between the identifying information of the first signal and the second signal. The first device illustratively determines whether the identifying information of the second signal corresponds to the identifying information of the first signal. In the illustrative embodiment, the first device determines whether the bed ID indicated by the second signal corresponds to the bed ID indicated by the first signal. If the identifying information of the second signal does not correspond to the identifying information of the second signal, the process returns to step 42. If the identifying information of the second signal does correspond to the identifying information of the second signal, the process proceeds to step 48.

In step 48, an ad-hoc network is established between the first and second devices. The first device illustratively permits formation of an ad-hoc network with the second device. In the illustrative embodiment, the bed communications device 14 permits formation of an ad-hoc network with the local communications device 16.

In the illustrative embodiment, IR signals are only communicated in a signal direction, from the local communications device 16 to the bed communications device 14. The bed communications devices 14 is illustratively configured to receive, but not to transmit IR signals. The IR communications circuitry 26 is illustratively embodied to include circuitry for receiving but not transmitting, IR signals. By requiring only circuitry for receiving IR signals on the bed communications device 14 the complexity and expense of the bed hardware and the power demand for bed communications can be reduced. In the illustrative embodiment, the local communications device 16 is configured to transmit and receive IR signals, but in some embodiments, may be configured only to transmit IR signals to minimize cost and complexity. In some embodiments, one or both of the local communications device 16 and the bed communications device 14 may include IR transmitters and IR receivers.

In the illustrative embodiment, the bed 12 communicates a first signal, embodied to include a Bluetooth signal, indicating the bed ID, and the local communications device 16 responds with a second signal, embodied to include an infrared signal indicating the bed ID as indicated by the first signal. In some embodiments, the local communications device 16 may be configured to prompt the bed 12 for the first signal, for example, by first sending a prompt signal embodied as an IR prompt signal. In some embodiments, the bed 12 may communicate the bed ID as the first signal as described above. In some embodiments, the IR prompt signal may indicate a unique identifier corresponding to the local communications device 16 and the bed 12 may receive the IR prompt signal and send a response signal, embodied as a Bluetooth signal, indicating the received unique identifier. The local communications device 16 may receive the response signal and form an ad-hoc network with the bed 12 upon confirmation that the received unique identifier corresponds to the sent unique identifier. In some embodiments, the prompt signal may be a Bluetooth signal and the response signal may be an IR signal.

In the illustrative embodiment, the bed 12 sends the first signal embodied as a Bluetooth signal and the local communications device responds with the second signal embodied as an IR signal. In some embodiments, the first signal may include an IR signal indicating the bed ID and the local communications device 16 receives the first signal and sends the second signal as a Bluetooth signal indicating the received bed ID to the bed 12 for confirmation of correspondence and formation of an ad-hoc network upon confirmation. In some embodiments, including those mentioned immediately above, the IR signals are only communicated in a signal direction, between the local communications device 16 to the bed communications device 14 and the communications circuitry 26, 36 of the respective bed communications device 14 and local communications device 16 may be correspondingly limited in arrangement to only transmit or receive IR signals as described.

In some embodiments, the bed communications device 14 may be embodied as a patient communications device mounted to or included in any patient care device, such as a patient lift, pump, vital signs monitor (e.g., EKG, ECG, EEG, respiration rate monitor, blood pressure monitor, pulse oximetry equipment), etc. and multiple patient communications devices may communicate with the local communications device to establish an ad-hoc network. In some embodiments, upon successfully establishing an ad-hoc network between multiple patient communications devices and the same local communications device 16, the local communications device 16 responsively configures the patient communications devices for direct communication with each other (when capably equipped, for example, when configured for communication with the same protocol).

Returning to FIG. 1, the network 300 illustratively includes various facility communications intercommunicated devices and processes, for example, medical records database (MMR) 310, communications circuitry 312 in communication with local communications devices 16, servers 316, local workstations 314, and workflow databases 318. In the illustrative embodiment, the workflow databases 318 are embodied to include at least one relational database for storing, maintaining, and accessing unique identification codes assigned to staff, equipment, locations, and other things of the facility in correspondence with each other. In the illustrative embodiment, the local communications device 116A is associated with room 100 by association within the relational database of the network 300, but may be directly associated by programming and/or other suitable methods.

As mentioned above, upon formation of an ad-hoc network between a bed 12 and a local communications device 16, the local communications device 16 provides communication between the network 300 and the bed 12. The bed 12 can communicate with the network 300 through the local communications device 16 to send and receive information therebetween. Communications made through local communications device 16 illustratively indicate an ID code unique to the specific local communications device 16 that is illustratively maintained with association by the network 300.

Figures 4, 5:
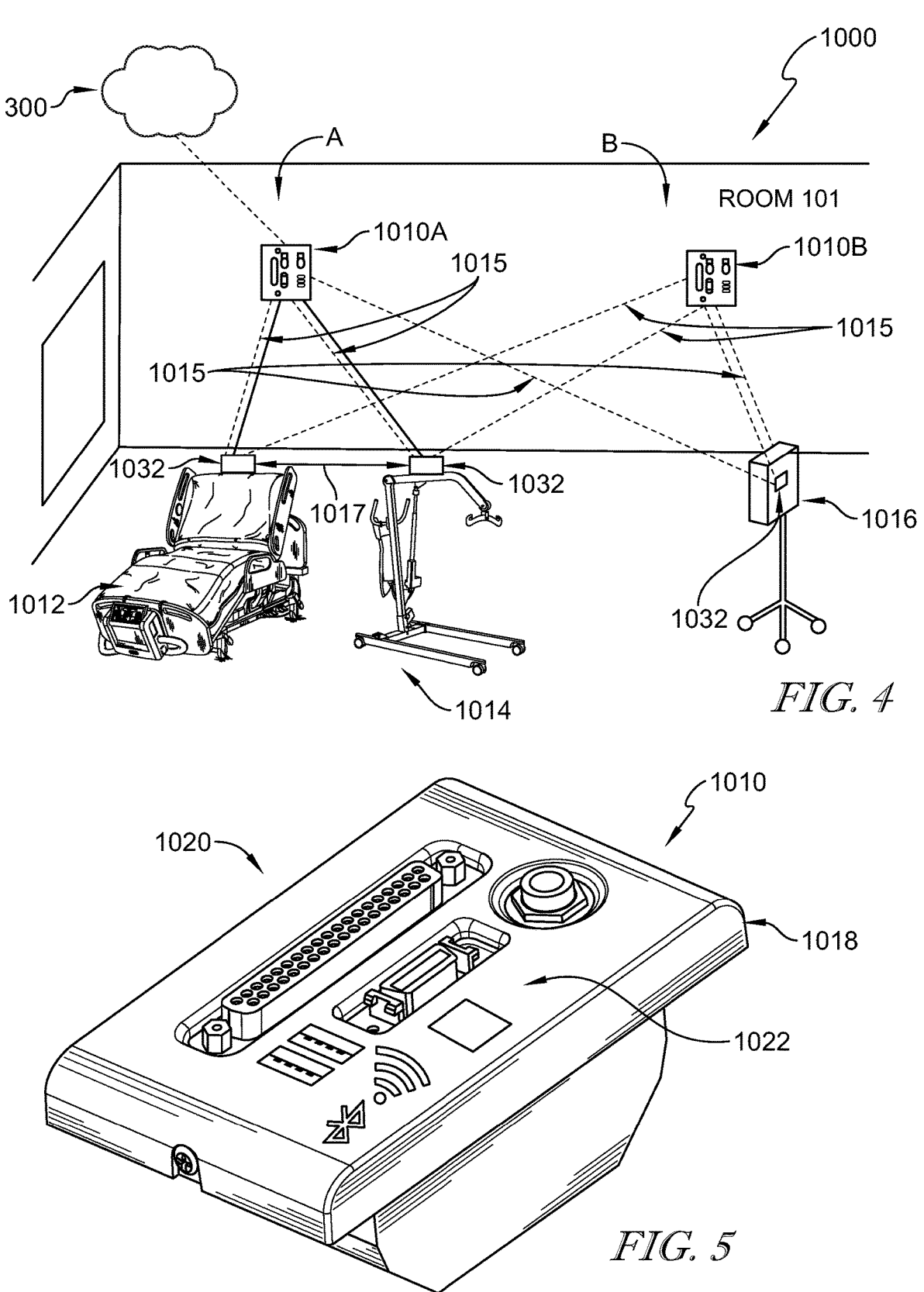
FIG. 4 is a perspective view of another illustrative embodiment of a patient care communications system providing communications between patient devices and a network of the care facility through communications hubs.
FIG. 5 is a perspective view of one of the communications hubs of FIG. 4.

Another illustrative embodiment of a patient care communications system 1000 for communication with the network 300 of the care facility is shown in FIG. 4. The patient care communications system 1000 is similar to the patient care communications system 10 and the disclosure of the patient care communications system 10 applies to the patient care communications system 1000, except in instances of conflict with the description of the patient care communications system 1000 below. The patient care communications system 1000 illustratively includes communication hubs (generally 1010, collectively 1010, and individually 1010A, 1010B) in communication with each other and with a number of patient devices 1012, 1014, 1016 arranged to communicate information with the communications hubs 1010. The patient devices 1012, 1014, 1016, sometimes referred to herein as patient care devices, can communicate information with the network 300 through the communications hubs 1010 while discriminating against certain communications, for example, based on relative location. Discriminating certain communications can enable fine location determination of the patent devices 1012, 1014, 1016 and/or adaptive connectivity between the network 300 and patient devices including those that use different communications platforms and/or protocols.

In the illustrative embodiment as shown in FIG. 4, the communications hubs 1010 are shown as being stationary within the care facility, illustratively located within sections A, B of the patient room 101. Patient room 101 is illustratively embodied as a shared patient room, and the sections A, B each indicate distinct areas of the room 101 that are generally considered exclusive to one of a pair of patients assigned to the shared room 101. Such rooms are sometimes referred to as semi-private rooms. The patient devices 1012, 1014 are illustratively located within section A and are associated with section A of the shared room 101, and the patient device 1016 is illustratively located within section B and is associated with section B of the shared room 101. Each communications hub 1010 is configured to be mounted to a wall of room 101 at a location corresponding to its respective section A, B.

In the illustrative embodiment, each communications hub 1010A, 1010B communicates with the patient devices 1012, 1014, 1016 that are located within their respective section A, B and discriminate against communication with devices that are not within their respective section A, B. The communications hubs 1010 themselves illustratively define the sections A, B in some embodiments. In the illustrative embodiment, the communications hubs 1010A, 1010B are in communication with each other to determine a preferred hub of the communications hubs 1010 for each patient device 1012, 1014, 1016.

In the illustrative embodiment shown in FIG. 4, the communications hubs 1010A, 1010B determine which among them is a preferred communications hub for each patient device 1012, 1014, 1016 based on their received signal strength from each patient device 1012, 1014, 1016 as explained in detail below. Although each communications hub 1010A, 1010B is within signal range of each patient device 1012, 1014, 1016, the patient device 1016 communicates device information with hub 1010B as its preferred hub (as indicated by the respective double line communications link 1015 between device 1016 and hub 1010B in FIG. 4), while being disregarded by hub 1010A; and the patient devices 1012, 1014 each communicate device information with hub 1010A as their preferred hub (as indicated by the respective double line communications link 1015 between devices 1012, 1014 and hub 1010A in FIG. 4), while being disregarded by hub 1010B. Each patient device 1012, 1014, 1016 illustratively communicates with the network 300 through its respective preferred hub, although the hub 1010B illustratively communicates with the network 300 through the hub 1010A as discussed below. In some embodiments, the hub 1010B may be in communication with the network 300 without communicating through the hub 1010A.

In the illustrative embodiment of FIG. 5, the communications hubs 1010 are configured to send and/or receive various types of signals for communication with the network 300 and the patient devices 1012, 1014, 1016. The communications hubs 1010 illustratively include a housing 1018 having various hardwired communication circuitry 1020 such as hardwired ports (e.g., parallel ports including standard 37 pin connections used in HILL-ROM® nurse call systems, serial ports, coaxials, universal serial bus (USB), SPI, I2C, UART, fiber optics, ethernet, other general pin input/output (GPIO), other analogue and/or digital ports, etc.) and various wireless communications circuitry 1022 for wireless communications (e.g., Bluetooth®, Zigbee®, Wi-Fi®, WiMAX, 3G and/or 4G technology, radio frequency (RF), infrared (IR), sonar, including different versions thereof (e.g., classic Bluetooth® and Bluetooth 4.0/low energy), and/or other wireless and/or mobile communications signal types and/or protocols).

In the illustrative embodiment, the communications hubs 1010 can communicate with the patient devices 1012, 1014, 1016 using any of the communications circuitry 1020, 1022 (including any of the their various ports, wired and/or wireless signals types, and/or wired and/or wireless protocols) to enable communications across diverse communication platforms of different patient devices 1012, 1014, 1016. For example, if the patient device 1012, embodied as a patient bed, is only enabled for Wi-Fi communications while the patient device 1014, embodied as a patient lift, is only enabled for Bluetooth communications, the communications hubs 1010 can communicate information with both patient devices 1012, 1014 in their respective connections (i.e., wireless protocols in this example). In another example the patent bed 1012 may be connected to one of the communications hubs 1010 by parallel or serial wired connection to a port while the lift 1014 is only enabled for Bluetooth communications, and the one communications hub 1010 can still communicate information with both patient devices 1012, 1014 through the respective wired and wireless connections.

Figure 6:
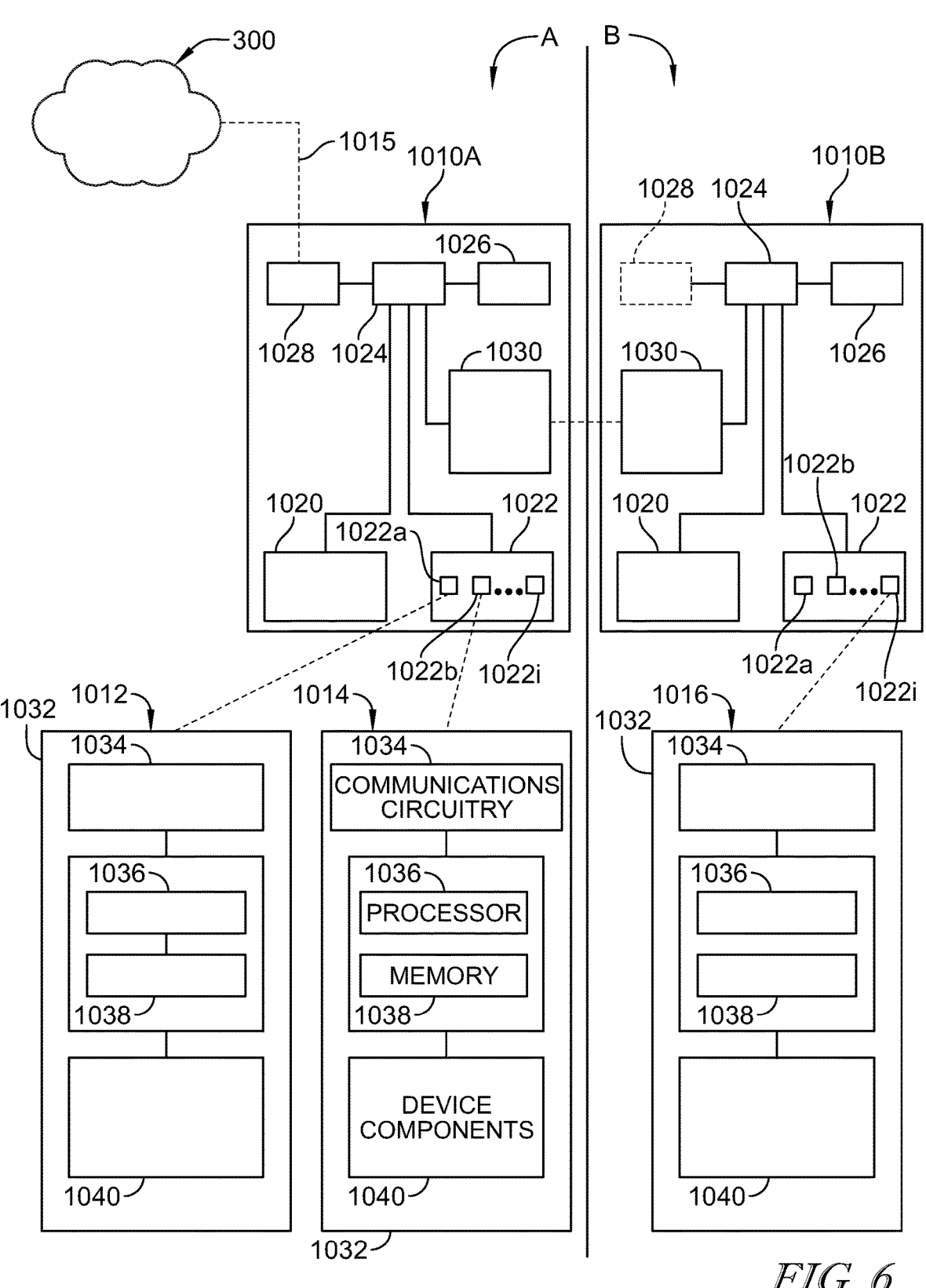
FIG. 6 is a diagrammatic view of the patient care communications system of FIG. 4 showing that communications hubs include communications circuitry for communication with various patient devices using a variety of signal types and/or protocols.

In the illustrative embodiment as shown in FIG. 6, the communications hubs 1010 each illustratively include a processor 1024, a memory device 1026 storing instructions for retrieval and execution on the processor 1024, and communications circuitry 1028, 1030 for communicating information between the processor 1024 and other devices. The memory device 1026 illustratively includes protocol stack(s) for providing a transport interface for communications between the patient devices 1012, 1014 and the network 300 (i.e., transport between the device protocol and the network protocol). In the illustrative embodiment as shown in FIG. 6, the communications circuitry 1028, 1030 each send and receive signals as directed by the processor 1024 to provide the transport interface between the network 300 and the patient devices 1012, 1014.

The communications hubs 1010 illustratively receive signals indicating device information from the patient devices 1012, 1014, 1016 using their respective base protocols. The communications hubs 1010 illustratively implement the appropriate protocol stack to provide the transport interface for communications between the patient devices 1012, 1014, 1016 and the network 300 as needed. In the illustrative embodiment, the communications hubs 1010 include protocol stacks to accommodate each of the variety of base protocols through which the patient devices 1012, 1014, 1016 communicate.

In the illustrative embodiment, the communications hubs 1010 provide the transport interface between the network 300 and the patient devices 1012, 1014, 1016 that have any mode of wireless and/or wired communication. The communications hubs 1010 illustratively provide a transport interface for communication between the patient devices 1012, 1014, 1016 themselves, for example, between the exemplary Wi-Fi of patient bed 1012 and the exemplary Bluetooth of patient lift 1014. In some embodiments, upon successful connection of multiple patient devices 1012, 1014, 1016 to the same communications hub 1010, the communications hub 1010 responsively configures those patient devices 1012, 1014, 1016 connected to the same hub 1010 for direct communication with each other when capably equipped (for example, a bed 1012, and lift 1014 both in section A and communicating with hub 1010A are configured to exchange information directly as indicated by arrows 1017 in FIG. 4, and the bed 1012 may for example communicate a patient weight as measured by a load scale of the bed 1012 to the lift 1014 for appropriate configuration), for example, when configured for communication with the same protocol. The communications hubs 1010 illustratively provide a transport interface between patient devices having different preferred hubs, for example, between the patient device 1016 and the patient devices 1012, 1014.

In some embodiments, the communications hubs 1010 may use a number of combined protocols (without an intermediary or transport protocol) to communicate information directly between the network 300 and each patient device 1012, 1014, and/or between the patient devices 1012, 1014, 1016 themselves, according to their base protocols. The communications hubs 1010 thus provide a common communications platform using the underlying communications capability of each device, and without requiring upgrading, replacement, and or customization of the software of each device 1012, 1014, 1016.

As show in FIG. 6, the wireless communications circuitry 1022 of each communications hub 1010 illustratively includes various interface circuitry 1022a, 1022b, . . . 1022i, that each are configured to accommodate different wireless signal types and/or protocols. The interface circuitry 1022a, 1022b, 1022i are illustratively embodied to independently include communications components such as antennas, receivers, transmitters, and/or signal conditioners (e.g., filters, amplifiers, converters, isolaters, etc.), but in some embodiments may share any number of components. By example, the patient bed 1012 illustratively communicates only in Wi-Fi and sends and receives Wi-Fi signals with Wi-Fi interface circuitry 1022a, and patient lift 1014 illustratively communicates only in Bluetooth and sends and receives Bluetooth signals with Bluetooth interface circuitry 1022b. The processor 1024 performs the appropriate protocol transport for the information received by the communications circuitry 1020, 1022 and sends signals according to the output protocol to the network 300 via the communications circuitry 1028 and/or to the appropriate patient device 1012, 1014 via the communications circuitry 1020, 1022.

In the illustrative embodiment as shown in FIG. 6, the communications hubs 1010A, 1010B each communicate with the network 300. The communications hub 1010A communicates with the network 300 via communications link 1015, while communications hub 1010B illustratively communicates with the network 300 through the communications hub 1010A. The communications circuitry 1030 illustratively sends and receives signals as directed by the processor 1024 with the communication circuitry 1030 of the communications hub 1010B.

In the illustrative embodiment, the communications hubs 1010A, 1010B communicate with each other via the network protocol. In some embodiments, the preferred hub of each patient device 1012, 1014, 1016 performs protocol transport for communications with its respective device, and/or the communications hub 1010A, 1010B that is sending communications to the other hub 1010A, 1010B determines the applicable protocol for communication between the hubs 1010, for example, to reduce multiple transport, the hub 1010A may send communications from the patient bed 1012 to the communications hub 1010A using the base protocol of the patient bed 1012. In some embodiments, the manner of protocol transport for each transmission scenario (considering e.g., whether to/from a patient device or the network 300, the patient device type, device location, communication protocol, information/communication type) may be partly or wholly predetermined and/or dynamically determined by the communications hubs 1010. In some embodiments, the communications hub 1010B may include its own communications circuitry 1028 (as shown in dashed line in FIG. 6) for communication with the network 300.

As shown in FIG. 6, the patient devices 1012, 1014, 1016 each illustratively include an operations module 1032 including communications circuitry 1034 for communicating with the communications hubs 1010, a processor 1036 for executing instructions stored on a memory device 1038, and device components 1040 for performing various device functions (e.g., sensors, actuators, pumps, fans, etc.). The processor 1036 of each patient device 1012, 1014, 1016 is illustratively embodiment as a main processor that controls each of device operation and communications. In some embodiments, device operation and communication may be performed by any number of hardware and/or software components that are partly and/or wholly shared.

Figure 7:
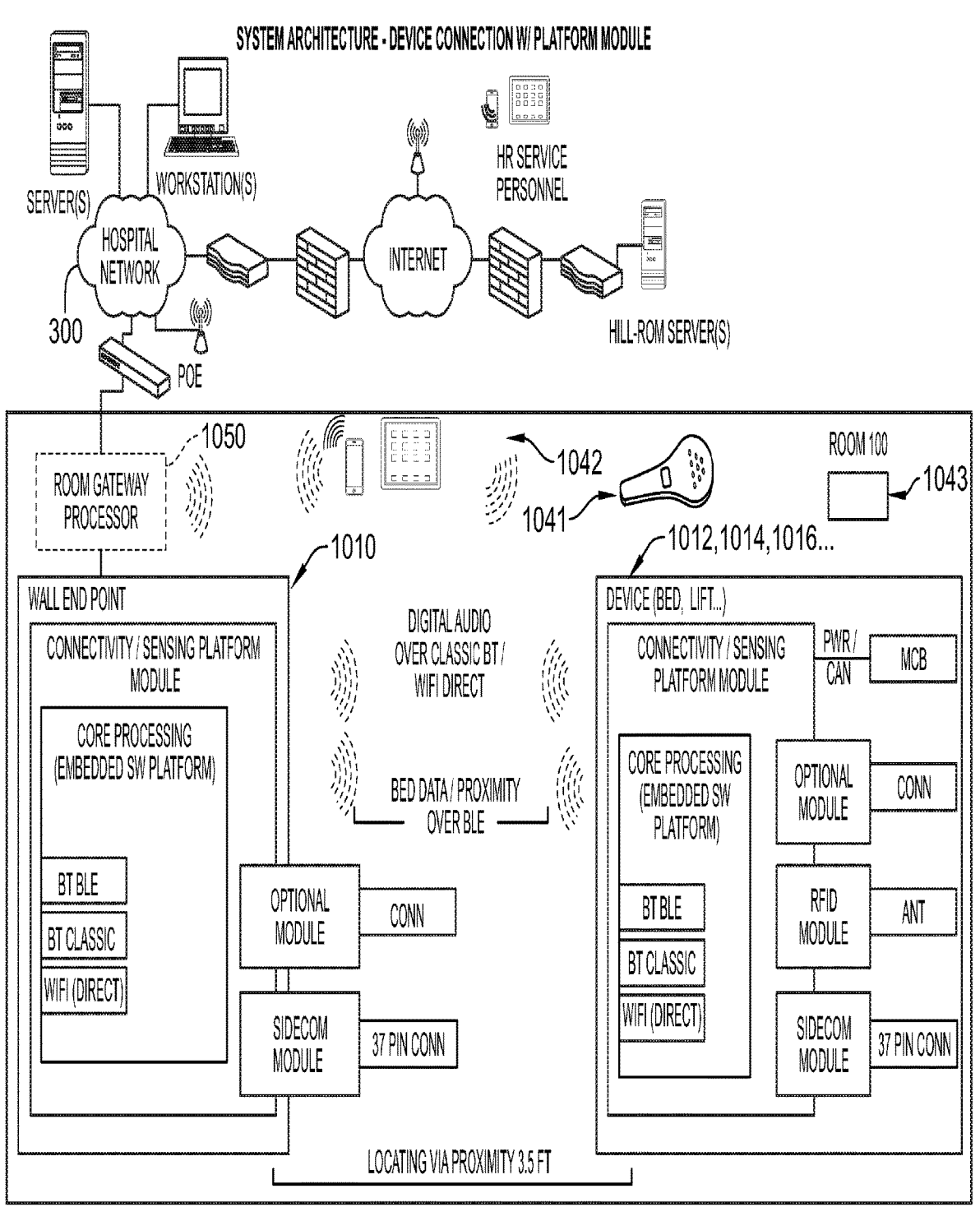
FIG. 7 is a diagrammatic view of the patient care communications system of FIGS. 4-6 showing that the system can optionally include a gateway for conducting local decision operations.
Figure 8:
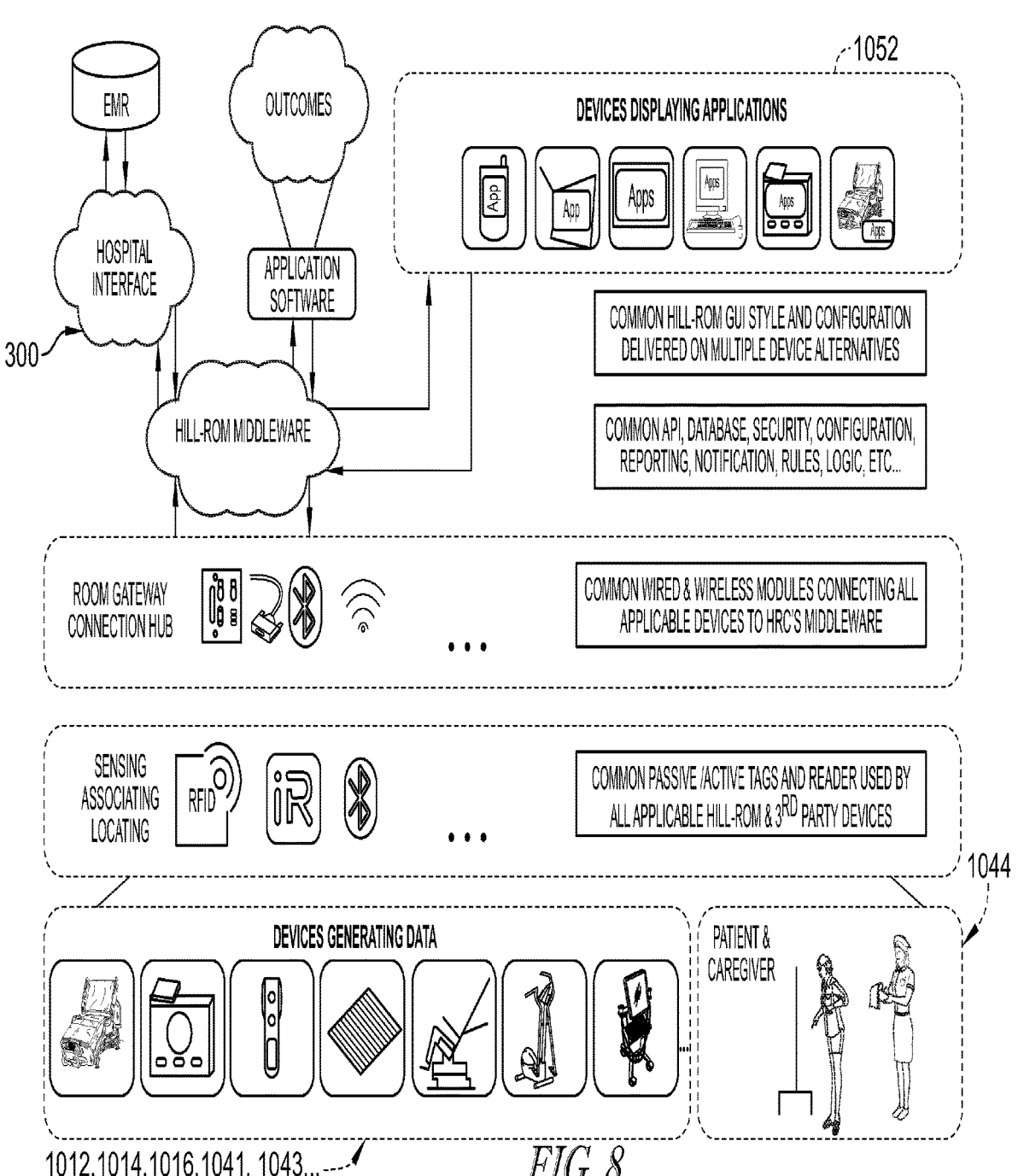
FIG. 8 is an illustrative depiction of the patient care communications system of FIGS. 4-7 primarily at the software level.
Figure 9:
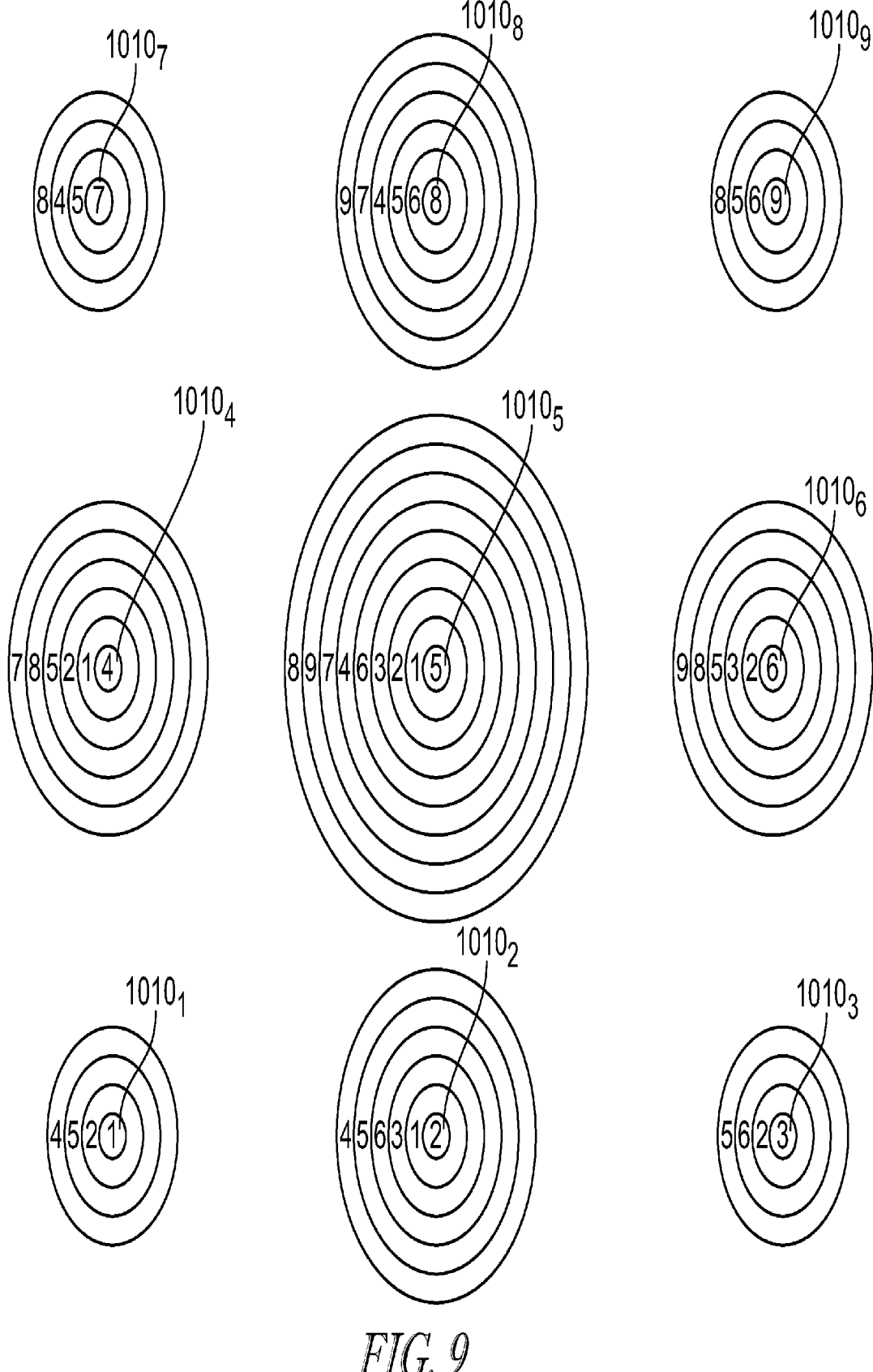
FIG. 9 is a plan view of an arrangement of communications hubs of the patient care communications system of FIGS. 4-8 showing that the communication hubs are in wireless communications with each other to form a mesh network.

Referring to FIG. 7, the patient care communications system 1000 can optionally include a gateway 1050 for providing localized decision support. In the illustrative embodiment, the gateway 1050 is arranged between the communications hubs 1010 and the network 300 and performs a variety of evaluation and decision functions for communications and operations support. The gateway 1050 illustratively conducts communications with each of the network 300 and the communications hubs 1010.

In the illustrative embodiment, the gateway 1050 performs localized decision support based on communications from each of the network 300 and the communications hubs 1010. In a network-driven example, the gateway 1050 can illustratively implement localized decision operations according to direction from the network 300. The gateway 1050 illustratively receives room commands from the network 300 indicating a desired room configuration for a particular patient, for example, a "fall risk" room configuration for a patient characterized as a fall risk. The gateway 1050 illustratively receives the desired room configuration ("fall risk") command from the network 300, determines the specific device configurations required to achieve the desired room configurations, and communicates device commands to the communications hubs 1010 indicating the specific device configurations. The communications hubs 1010 communicate the specific device configurations to each patient device 1012, 1014, 1016 according to its communications standards as discussed above.

Continuing with the fall risk example mentioned above with reference to FIG. 7, a computer device on the network 300 illustratively issues a "fall risk" room command to the gateway 1050 in response to one or more user inputs, such as at a remote computer or station (e.g., EMR computer, master nurse station, ADT computer, etc.). In response to the "fall risk" room command, the gateway 1050 illustratively determines that the appropriate "fall risk" room configuration requires device commands that configure the patient bed 1012 to require a patient lift 1014 to be present (e.g., within in the same section A, B as the patient bed 1012) when bed side rails are lowered or else a fall alarm shall be issued. The gateway 1050 communicates the device commands to the communications hub 1010 for communication to the patient bed 1012. In this example, the communications hub 1010 illustratively determines the presence of the patient lift 1014 (e.g., within in the same section A, B as the patient bed 1012) according to whether the bed lift 1014 communicates with the communications hub 1010 as its preferred hub as mentioned above and discussed in detail below. Thus, the communications hub 1010 itself can implement certain device commands as appropriate. The gateway 1050 illustratively conducts localized decision operations using network-room level communications.

In a room-driven example, the gateway 1050 can conduct localized decision operations based on patient device information. The gateway 1050 illustratively receives device information from any of the patient devices 1012, 1014, 1016. For example, the gateway 1050 illustratively receives communication from the patient bed 1012 that a patient is occupying the bed and that a bed side rail is in a lowered position (e.g., indicating that the patient occupying the patient bed 1012 may intend to exit the bed). Following the above "fall risk" example, the gateway 1050 illustrative issues a command for local alarm (e.g., illuminate attention indicator light on patient bed 1012) in response to the indication that the bed side rail is lowered, but does not communicate with the network 300 to issue an system alarm requiring caregiver attention (e.g., nurse call) because the gateway 1050 receives indication from the patient lift 1014 that it is located within the relevant proximity of the patient bed 1012 (illustratively, within section A). The gateway 1050 illustratively conducts localized decision operations using room level communications.

In some embodiments, the communications hubs 1010 may be in communication with various devices such as telemetry devices, window shades, television, temperature/humidity control, room lighting, etc. and may operate the various devices to predetermined configurations upon detection of event scenarios such as a patient bed entering the room 100, detection of a patient, etc. For example, upon entrance of a patient into the room 100, the communications hubs 1010 may operate the lighting in the room for a default moderate light setting.

In the illustrative embodiment, a single gateway 1050 conducts localized decision operations for a single communications hub 1010, but in some embodiments, one or more gateways 1050 may provide local decision operations for one or more communications hubs 1010, for example, a single gateway 1050 may conduct localized decision operations for each room of the care facility including for all communications hubs 1010 therein. In some embodiments, the gateway 1050 may be combined in hardware and/or software components with one or more communications hubs 1010.

The patient devices 1012, 1014, 1016 have been illustratively described as respective patient beds, patient lifts, and patient fluid pumps, but in some embodiments may include any number and/or type of patient devices such as vital signs monitors, exercise equipment, passive motion machines, etc. As shown in FIG. 7, the system 1000 illustratively includes another patient device embodied as a wireless communications device 1041 in communication with the communications hubs 1010. The wireless communications device 1041 includes a wireless speaker configured to play audio received from the communications hubs 1010 from the network 300 (for example, voice communications over a nurse call system) and/or from an in-room television, and a nurse call button for communicating a call to the network 300 for transmission over a nurse call system. In the illustrative embodiment, the wireless communications device 1041 communicates with the communications hubs 1010 using Bluetooth low energy communications, but in some embodiments may communicate with the communications hub 1010 by any suitable manner Device 1041 is sometimes referred to as a pillow speaker.

In the illustrative embodiment, the wireless communications device 1041 includes a solar cell for converting light energy into electrical power and a battery for storing power from the solar cell for use by the wireless communications device 1041, but in some embodiments may include a battery charging system. The system 1000 illustratively includes a number of dedicated wireless nurse call switches 1043 (for example, near the bath, shower, and/or bedside) in communication with the communications hubs 1010 and each having a solar cell and battery for dedicated nurse call function. In some embodiments, the communications hubs 1010 may periodically confirm connectivity with the wireless communications device 1041 and/or the nurse call switches 1043 to provide continual communications availability. In some embodiments, the wireless communications device 1041 may include a microphone and circuitry for audio transmission from the patient to the network 300 to allow voice communications with caregivers.

As shown in FIG. 7, the system 1000 illustratively includes another patient device embodied as a display device 1042 for display of information related to the patient, the room, the patient devices, etc. In the illustrative embodiment, the display device 1042 is a tablet computer, but in some embodiments may be any suitable graphical display device and/or graphical user interface. The display device 1042 illustratively communicates with each of the network 300 and the other patient devices 1012, 1014, 1016, 1041 through the communications hubs 1010.

The display device 1042 illustratively receives information from the network and/or other patient devices 1012, 1014, 1016, 1041 through the communications hubs 1010 and provides graphical display and interface for user interaction as suggested in FIG. 7. For example, device information such as device operating parameters for the patient bed 1012 are illustratively presented in graphical form on the display device 1042 and a caregiver can illustratively operate the display device 1042 to change the firmness of an inflatable mattress of the patient bed 1012, can observe the weight of a patient occupying the patient bed 1012 as measured by the bed's load scale system, and/or observe battery power levels of the patient devices $1012$, $1014$, $1016$, $1041$.

In some embodiments, the display device $1042$ may be configured to display and/or operate other patient devices that are in communication with the communications hubs $1010$ such as telemetry devices, window shades, television, temperature/humidity control, room lighting, etc. In the illustrative embodiment, the display device $1042$ is operable to provide full device functionality control of the patient devices, but in some embodiments, may provide limited functionality control. In some embodiments, the display device $1042$ may be accessible only to caregivers and not to patients and/or visitors, for example, by passcode, and/or may have limited controls for non-caregivers.

The display device $1042$ illustratively receives and displays information from the network $300$ as suggested in FIG. $7$. For example, the display device $300$ may receive patient identification information such as date of birth, gender, medical records, laboratory results for display and/or manipulation through the communications hubs $1010$. The display device $1042$ illustratively displays the number and location information of patient devices within the room and communicating with the communications hubs $1010$. The display device $1030$ illustratively permits configuration of the communications hubs $1010$ (and/or the gateway $1050$ when included), for example, manual assignment of patient devices to communicate with one of the communications hubs $1010A$, $1010B$ as the preferred hub. In the illustrative embodiment, the display device $1042$ is permanently located within room $100$, but in some embodiments, may be located at a nurse station and/or be portable throughout the care facility. In some embodiments, the display device $1042$ may be connectible to the communications hubs $1010$ by a cable for communications therewith. In some embodiments, the display device $1042$ and/or the wireless communications device $1041$ may communicate with the gateway $1050$ and/or the network $300$ directly.

As shown in FIG. $8$, an illustrative depiction of the system $1000$ is shown primarily at the software level. In the illustrative embodiment, the network $300$ includes a hospital interface which communicates with various systems through middleware. The middleware is illustratively implemented between the network $300$ function and the gateway $1050$ functions (and/or communications hubs $1010$ in embodiments that do not include the gateway $1050$). Additional display device applications $1052$ communicate with network $300$ through the middleware to generally provide consistent graphical user interface formats, systems, and/or styles and/or consistent programming interfaces, database, security, configuration, reporting, notification, rules, logic, etc. In the illustrative embodiment, particular software implementation may be conducive to certain articulated structural arrangements described herein, but in some embodiments, software and/or hardware may be arranged in any suitable manner, and/or according to the particular needs of the care facility.

As mentioned above, the patient care communications system $1000$ is illustratively arranged for local network communication between communications hubs $1010$ including device locating, such as real time locating as shown in FIGS. $9$ and $10$. Referring to FIG. $9$, a plurality of communications hubs (generally $1010$, collectively $1010$, and individually $1010_{1-9}$) are shown from overhead in various states of communication with each other. Each communications hub $1010$ is illustratively in communication with those other communications hubs $1010$ based on proximity, as indicated by the labeled circles around the hubs $1010$.

For example, as shown in FIG. $9$, the communications hub $1010_1$ is illustratively near to and is in communication with each of hubs $1010_2$, $1010_4$, $1010_5$ as indicated by the labeled circles 2, 4, 5 surrounding the hub $1010_1$. Comparably, the communications hub $1010_2$ is illustratively near to and is in communication with each of hubs $1010_1$, $1010_3$, $1010_6$, $1010_5$, $1010_4$ as indicated by the labeled circles 1, 3, 6, 5, 4, surrounding the hub $1010_2$. Comparably, the communications hub $1010_5$ is illustratively near to and in communication with each of hubs $1010_1$, $1010_2$, $1010_3$, $1010_6$, $1010_4$, $1010_7$, $1010_9$, $1010_8$ as indicated by the labeled circles 1, 2, 3, 6, 4, 7, 9, 8 surrounding the hub $1010_5$. In the illustrative embodiment, the communications hubs $1010$ can form a mesh topology, but in some embodiments may include any of a hub-and-spoke, star, ring, token ring, bus, and/or tree topology. In the illustrative embodiment as shown in FIG. $9$, the communications hubs $1010$ are arranged in a square framework (shown from overhead). The arrangement of the communications hubs $1010$ is illustrative and in some embodiments, the communications hubs $1010$ may be arranged in any suitable manner relative to each other.

In the illustrative embodiment shown in FIG. $9$, only communications hub $1010_7$ is in direct communication with the network $300$, and all other hubs $1010_{1-6, 8, 9}$ communicate with the network $300$ through the hub $1010_7$. Each communications hub $1010$ is illustratively in communication with hub $1010_7$ either directly and/or indirectly through other hubs $1010$. For example, the hub $1010_8$ is in direct communication with the hub $1010_7$ as illustrated by the numbered ring 7 around the hub $1010_8$. Hub $1010_3$ is illustratively in indirect communication with hub $1010_7$ through any number of connections, for example, through hub $1010_5$ and/or through hubs $1010_{2, 4}$. In the illustrative embodiment, the communications hubs $1010$ collectively determine the preferred communications routing, but in some embodiments communications routing may be partly or wholly predetermined.

In the illustrative embodiment as shown in FIG. $10$, an overhead view of the communications hubs $1010$ is shown. Each communications hub $1010$ includes a signal meter $1054_{1-9}$ configured to measure the strength of received signals. The communications hubs $1010$ of FIG. $9$ are shown without the labeled circles indicating intercommunication. The system $1000$ illustratively includes another patient device, embodied as a locator tag $1044$ carried by a caregiver. The locator tag $1044$ is illustratively embodied as a passive RFID tag that receives energy from RFID signals of the communications hubs and broadcasts a tag identification code in response, but in some embodiments may communicate with hubs $1010$ by any suitable signal type and/or protocol. The tag identification code is illustratively associated with a specific caregiver by the network $300$.

Instead of the labeled circles as shown in FIG. $9$ indicating intercommunication between the hubs $1010$, in the illustrative embodiment shown in FIG. $10$ the certain hubs $1010_{1, 2, 3, 5}$ include a signal ring $1046$ that indicates communication with the locator tag $1044$. FIG. $10$ shows a table $1048_{1, 2, 3, 5}$ next to each of the hubs $1010_{1, 2, 3, 5}$ that identifies the strength (dB) of the signal received by the respective hub $1010_{1, 2, 3, 5}$ from the locator tag $1044$ as measured by the respective signal meter $1054_{1, 2, 3, 5}$. Each hub $1010_{1, 2, 3, 5}$ illustratively receives a signal from the locator tag $1044$ and measures the strength of the received signal. Each hub $1010_{1, 2, 3, 5}$ communicates the strength of its received signal to the other hubs $1010$ and collectively the hubs 1010 deem the hub 1010 with the highest signal strength as the preferred hub for the locator tag 1044. In the illustrative embodiment, the preferred hub for locator tag 1044 is hub 1010₂ that illustratively has a signal strength of −60 dB.

Figure 10:
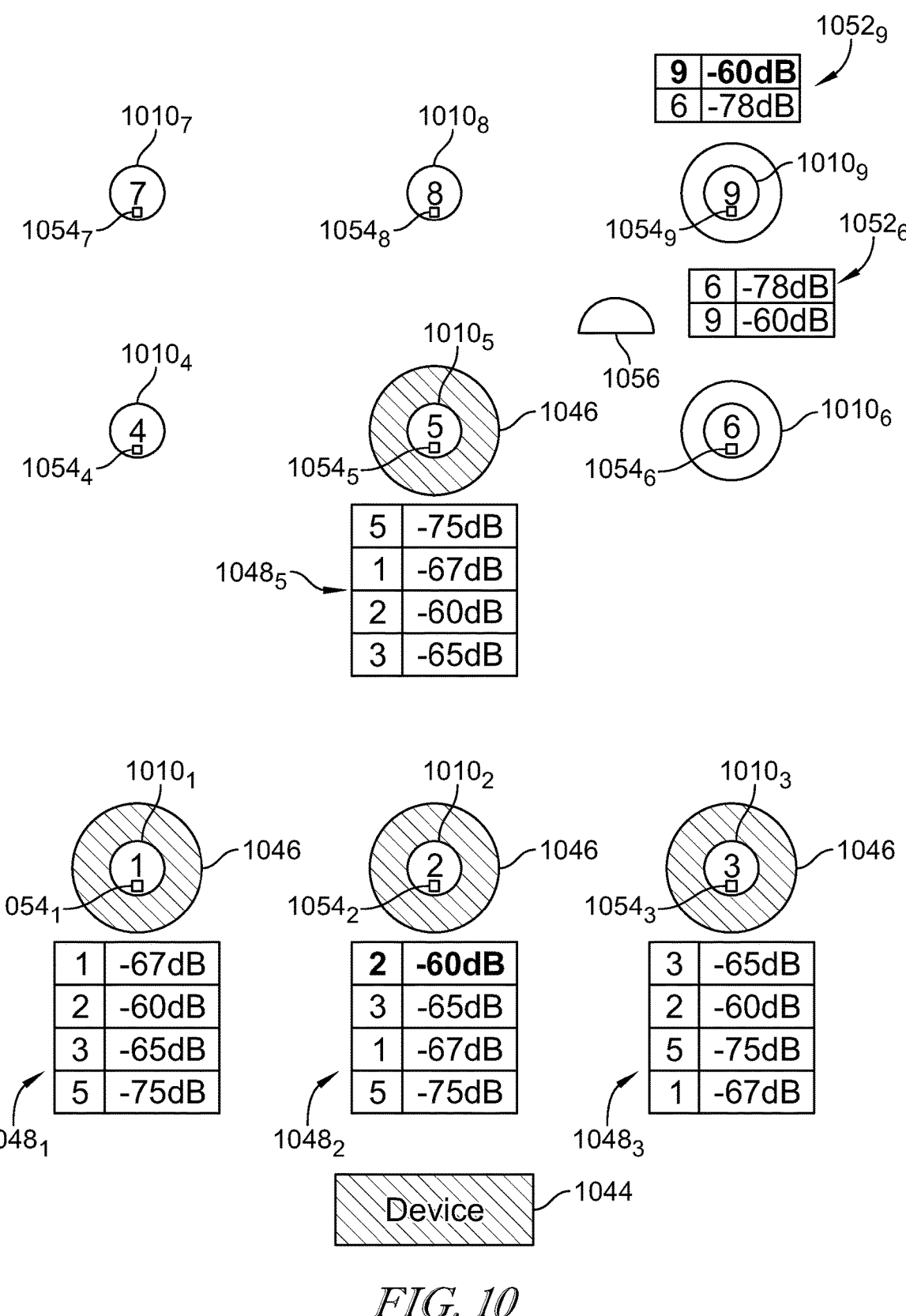
FIG. 10 is a plan view of the arrangement of communications hubs of FIG. 9 showing that the communications hubs determine a preferred communications hub for communications with a patient device based on the received signal strength indication.

In the illustrative embodiment as shown in FIG. 10, in response to the determination of the preferred communications hub 1010, the preferred hub (illustratively 1010₂) serves at the endpoint for patient device communication. The preferred hub (illustratively 1010₂) configures itself for direct communication with the locator tag 1044, while the other communications hubs 1010₁, ₃₋₉ configure themselves to disregard direct communications from the locator tag 1044. The locator tag 1044 illustratively communicates with any of the communications hubs 1010 and the network 300 through the preferred hub (illustratively 1010₂).

In the illustrative embodiment as shown in FIG. 10, the communications hubs 1010 continually re-designate the preferred hub based on the signal strength as discussed above. As the locator tag 1044 moves throughout the communications hubs 1010 (for example, as a caregiver carrying locator tag 1044 moves throughout a room of the care facility), the received signal strengths for each hub illustratively change with proximity to the locator tags 1044 and the greatest signal strength is deemed the preferred hub for any location. The preferred hub 1010 corresponds to the caregiver's location in the healthcare facility. In some embodiments, the communications hubs 1010 may periodically re-designate the preferred hub, may re-designate the preferred hub on loss of communication between the preferred hub and the locator tag 1044, and/or may re-designate the preferred hub upon the received signal strength by the preferred hub falling below a threshold value.

In the illustrative embodiment as shown in FIG. 10, the system 1000 can accurately determine and track the location of the locator tag 1044 and therefore, the location of the caregiver transporting the tag 1044. In the illustrative embodiment, the preferred hub illustratively communicates its selection as the preferred hub to the network 300 and/or to the gateway 1050 for tracking. In a given patient room, tracking the preferred hub can provide additional resolution as to the places in the patient room that the caregiver enters.

As shown in FIG. 10, the system 1000 illustratively includes another patient device embodied as another locator tag 1056. The locator tag 1056 is illustratively attached to a caregiver's clothing on the caregiver's chest and the caregiver is illustratively facing in the vertical direction (as shown in the overhead view in FIG. 10) as indicated by the curvature on the top side of the semi-circle symbol for locator tag 1056. FIG. 10 shows a table 1052₆, ₉ next to each of the hubs 1010₆, ₉ that identifies the strength (dB) of the signal received by the each hub 1010₆, ₉ from the locator tag 1056 as measured by the respective signal meter 1054₆, ₉. In the illustrative embodiment, the locator tag 1056 is positioned with equal distance from each of the communications hubs 1010₆, 1010₉, but the signal strength measured by hub 1010₉ is greater because the caregiver's body (illustratively represented by the flat side of the symbol for locator tag 1056) at least partly impedes direct line of sight with the communications hub 1010₆.

In some embodiments, the communications hubs 1010 may communicate to define specific areas such as patient bed areas and/or handwashing zones for use in event based patient care monitoring. By defining specific zones, the system 1000 can provide a level of automated event monitoring, for example, requiring entrance into a handwashing zone after exposures to potentially contaminated areas and generating/silencing alarms in response to the tracking.

In the illustrative embodiment, the communications links 1015 are embodied as Bluetooth® Low Energy (BLE), but in some embodiments may include any suitable type of wireless communications such as Bluetooth®, Zigbee®, Wi-Fi®, WiMAX, etc., mobile communications technologies such as 3G or 4G technology, radio frequency (RF), and or other wireless and/or mobile communications protocols. In some embodiments, the communications hubs 1010 may periodically confirm connectivity with any wireless devices including the patient device to provide continual communications availability.

As shown in FIGS. 11A, 11B, and 12A-12C, another illustrative embodiment of the communications hub 2010 of the system 1000 includes various connectivity features. The communications hub 2010 is similar to the communications hub 1010 and the disclosure of the communications hub 1010 applies to the communications hub 2010 except in instances of conflict with the description of the communications hub 2010. As shown in FIG. 11A, the communications hub 2010 illustratively includes a housing 2012 that encloses various components. The housing 2012 includes various input and/or output ports 2015 projecting therethrough for connections with other devices and/or systems. The ports 2015 illustratively include a female 37-pin connector 2016 for connection with a nurse call cable extending from patient bed 12, a male 37-pin bed connector 2018 for connection with a third party nurse call system (e.g., pass through), a 20-pin pillow speaker connector 2020 for connection with a 20-pin pillow speaker, and a ¼ inch jack receiver 2022 for connection with ¼ inch jack of a generic alarm cable extending from a respective patient care device, each arranged on a front wall of the housing 2012. The housing 2012 illustratively includes an IR sensor 2024, a nurse call button 2026 (indicated as a cancel button, that can be depressed to place and to cancel a nurse call request), and a multi-color LED status indicator 2028, also each on the front wall of housing 2012. As shown in FIG. 11B, the ports 2015 illustratively include an HDMI output port 2030, and a pair of USB ports 2032 arranged on a side wall of the housing 2012. A rear cover 2034 is illustratively secured to a rear of the housing 2012 to enclose circuitry within housing 2012 and support connectors thereon as discussed below.

Figures 12A, 12B, 12C:
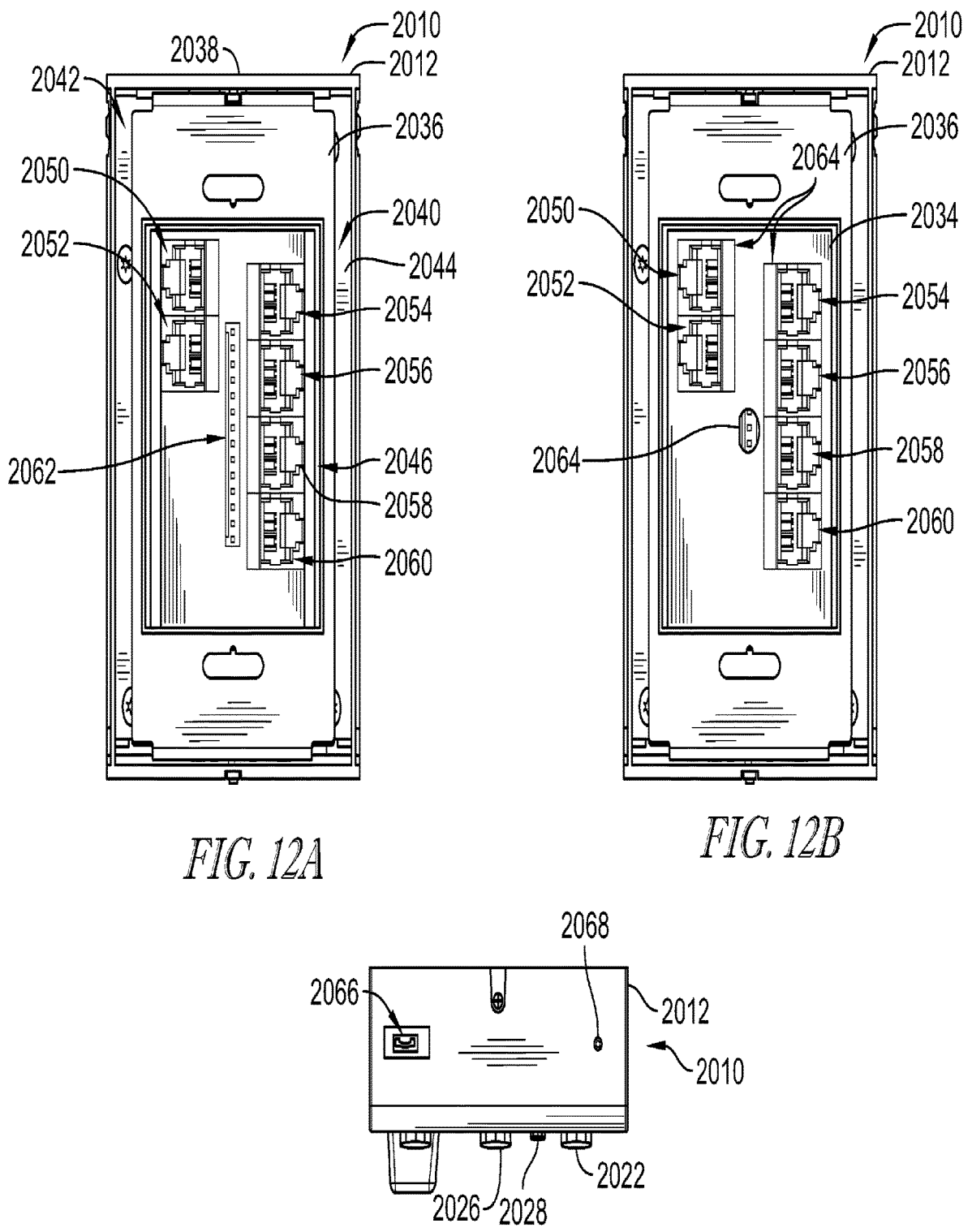
FIG. 12A is a rear elevation view of the communications hub of FIGS. 11A and 11B.
FIG. 12B is rear elevation view of the communications hub of FIGS. 11A, 11B, and 12A including a rear panel cover secured thereto.
FIG. 12C is a top plan view of the communications hub of FIGS. 11A-12B.

As shown in FIG. 12A, the housing 2012 illustratively includes a mounting bracket 2036 arranged on the rear side for mounting the communications hub 2010 and for receiving rear cover 2034 therethrough. As best shown in FIG. 12A, the housing 2012 illustratively includes an outer shell 2038 that defines an interior housing that receives an inner housing 2040. The outer shell 2038 illustratively encloses the front, top, bottom and sides of the inner housing 2040 and defines a rear opening 2042. The inner housing 2040 illustratively includes a rear plate 2044 covering the rear opening 2042 of the outer shell 2038 to receive the mounting bracket 2036 secured thereto.

As shown in FIG. 12A, the mounting bracket 2036 includes an opening 2046 defined therethrough to expose rear connections 2048. The rear connections 2048 include connection ports 2050, 2052, 2054, 2056, 2058, 2060, 2062. The connection ports 2050-2060 are each embodied as RJ-45 connectors for connection with a Power over Ethernet module (through port 2050), upstream data connections (through port 2052), downstream data connections (through port 2054), next generation room stations (through port 2056), a multi-segment dome light (8-segment, through port 2058), and a next generation wall switch (through port 2060). The connection port 2062 is embodied as a 14-pin entertainment connector for connection with entertainment controls, for example, low voltage controls for television, radio, and/or room lighting.

As shown in FIG. 12B, the rear cover 2034 includes openings 2064 through which the connection ports 2050-2060 and 2062 can receive cable connections while the rear cover 2034 is attached with the mounting bracket 2036. As shown in FIG. 12C (having the rear cover 2034 removed), the housing 2012 illustratively includes a micro USB slot 2066 and a reset button 2068 arranged on a bottom wall. The communications hub 2010 is illustratively adapted to conduct operations as disclosed above using the various ports 2015 and connections. In some embodiments, the communications hubs 2010 may include any number and/or configuration of communications connections, ports, components, etc for conducting operations.

Figure 13:
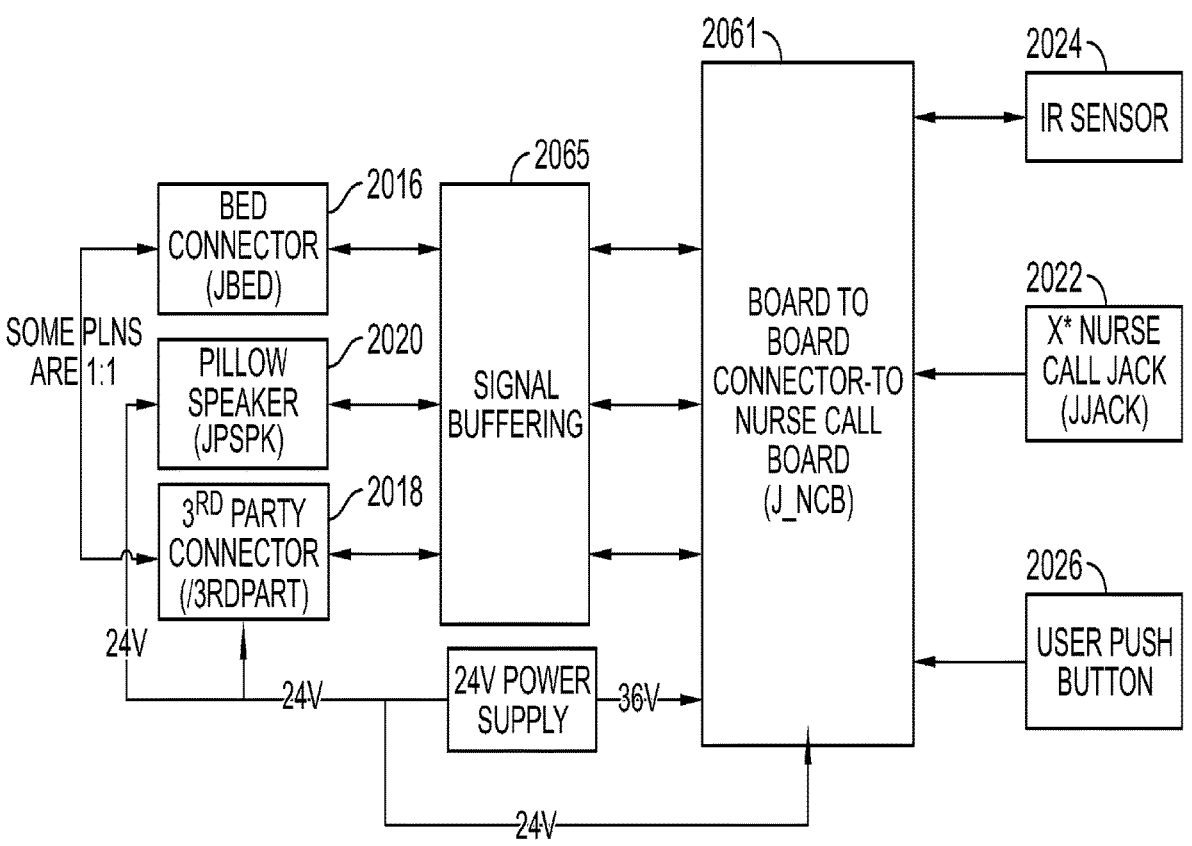
FIG. 13 is an exemplary block diagram shows signal connectivity for various connections of the communications hub of FIGS. 11A-12C.

Referring to FIG. 13, an exemplary block diagram of the signal connectivity of the communications hub 2010 is shown. In the illustrative embodiment, the communications hub 2010 includes a board-to-board connector 2061 which communicates with the nurse call system of the network 300. The board-to-board connector 2061 and each of the bed connector (e.g., 2016), pillow speaker connector (e.g., 2020), and third party connector (e.g., 2018) illustratively communicate through a signal buffering module 2065. The IR sensor 2024, jack receiver 2022, and nurse call button 2026 each illustratively communicate directly with the board-to-board connector 2061. In some embodiments, any number and/or type of signal conditioning modules may be applied to various board communications.

Figure 14:
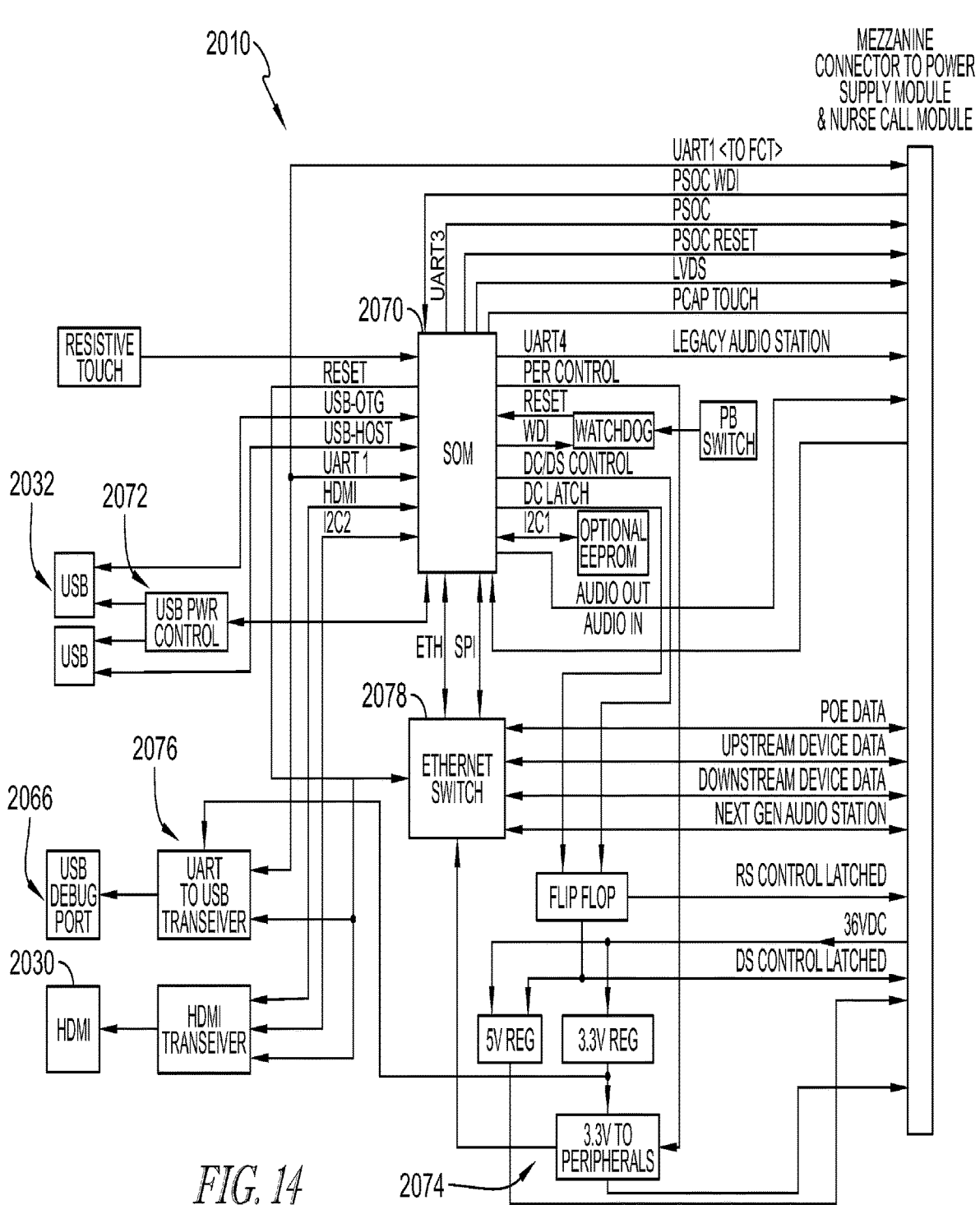
FIG. 14 is an exemplary circuit schematic of the communications hub of FIGS. 11A-13.

Referring now to FIG. 14, an exemplary circuit schematic of the communications hub 2010 is shown. The communications hub 2010 illustratively includes a system on a module (SOM) 2070 communicating with other systems and devices as discussed, directly and/or through various power controllers (e.g., power controller 2072, voltage regulators 2074), transmitter/receivers (e.g., transceivers 2076), switches (e.g., Ethernet switch 2078), and/or other signal management circuitry for performing communications hub operations. The SOM 2070 is illustratively equipped with a processor (e.g., iMX6, 1 GHz, 512 MB RAM, Audio Codec, 70C, LINUX, 200-pin, storage: 512 MB and/or 8 GB eMMC) with wireless capabilities (e.g, Wi-Fi 802.11 a/b/g/n with MIMO+Bluetooth 4.0/BLE). In some embodiments, the SOM 2070 may include an audio storage CODEC and/or any suitable processor and/or component arrangement.

Figure 15:
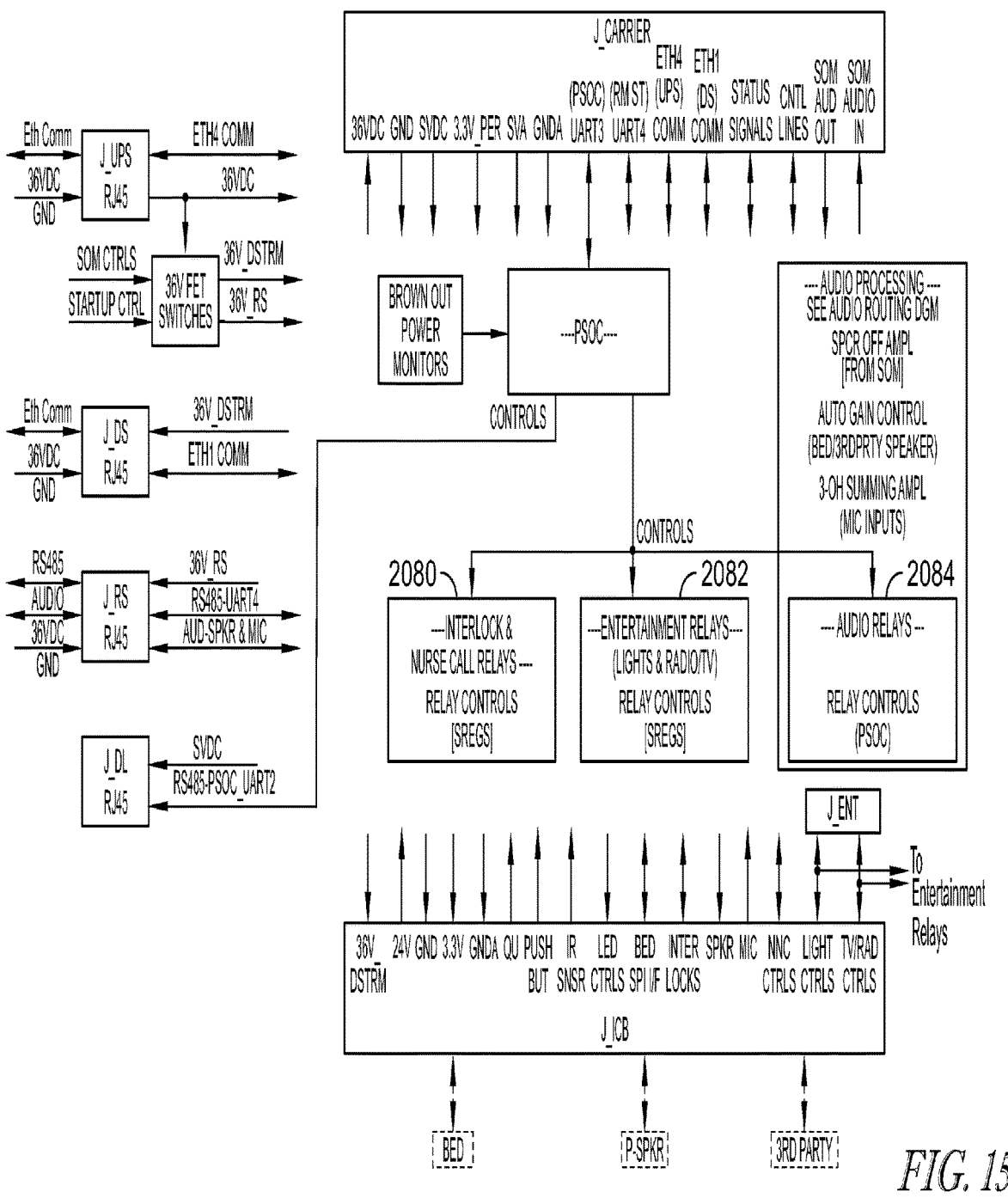
FIG. 15 is exemplary block diagram of the board level of various communications, control, power, and entertainment lines of the communications hub of FIGS. 11A-14.

FIG. 15 shows an exemplary board level block diagram of the communications hub 2010 including connection of the RJ-45 connectors, power, various communications inputs/outputs, various control lines, and entertainment connections between the communications hub 2010 and the nurse call board, bed, pillow speaker, third party nurse call system, and/or other system and devices, as well as control relays including interlock and nurse call relays 2080, entertainment relays 2082 (e.g., room lights, radio, television), and audio relays 2084. The communications hubs 2010 illustratively include a programmable system on a chip (PSoC) equipped with one or more of built in SPI, UART, I2C interfaces, and/or digital and/or analog I/Os, etc. Although not necessarily depicted in FIGS. 13-15, in some embodiments, the communications hub 2010 may include various circuitry for wireless communications with any of patient devices and/or network 300.

Figure 16:
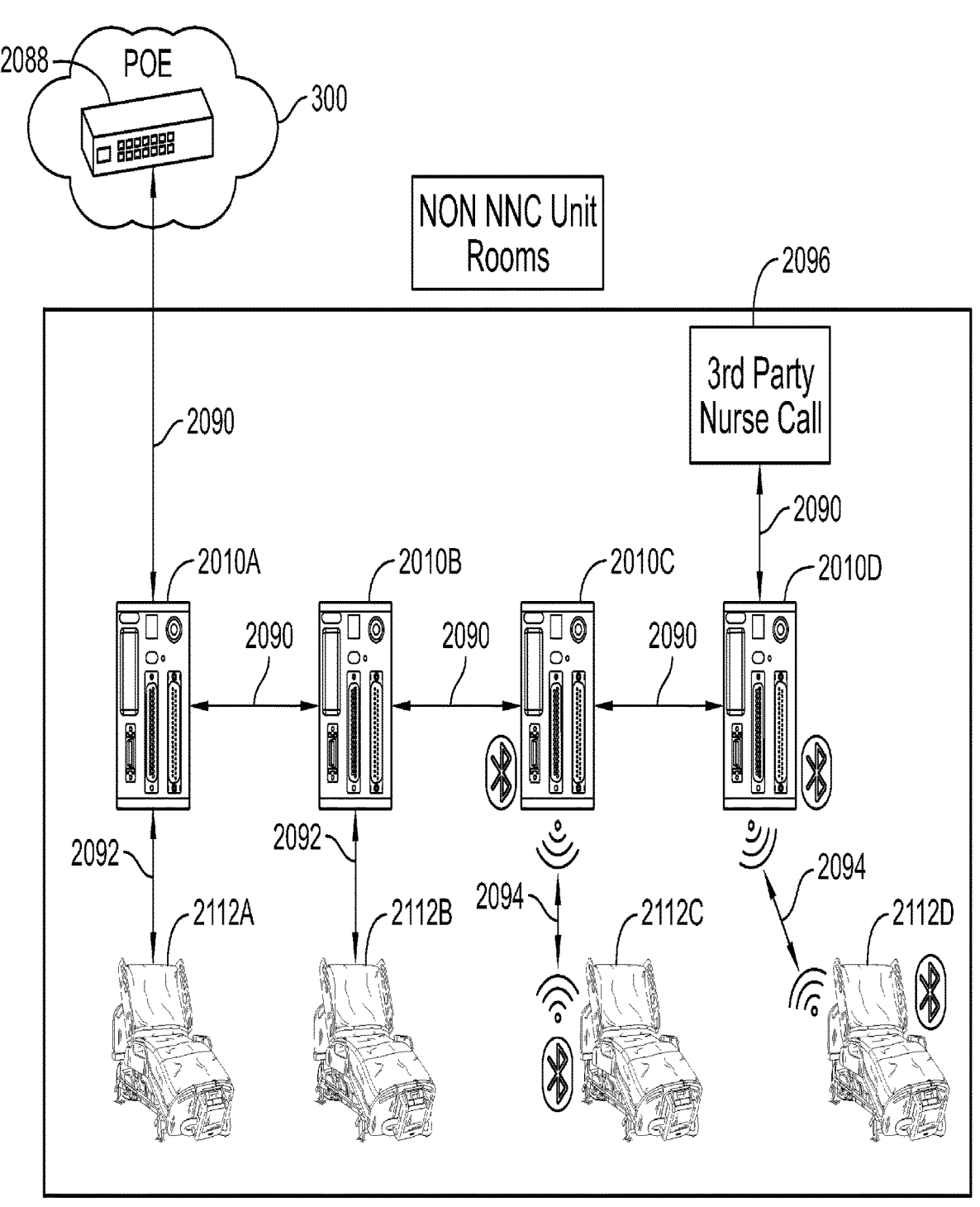
FIG. 16 is a diagrammatic arrangement of a number of communications hubs configured for use in a room of a care facility which is not equipped with a preferred nurse call system.
Figure 17:
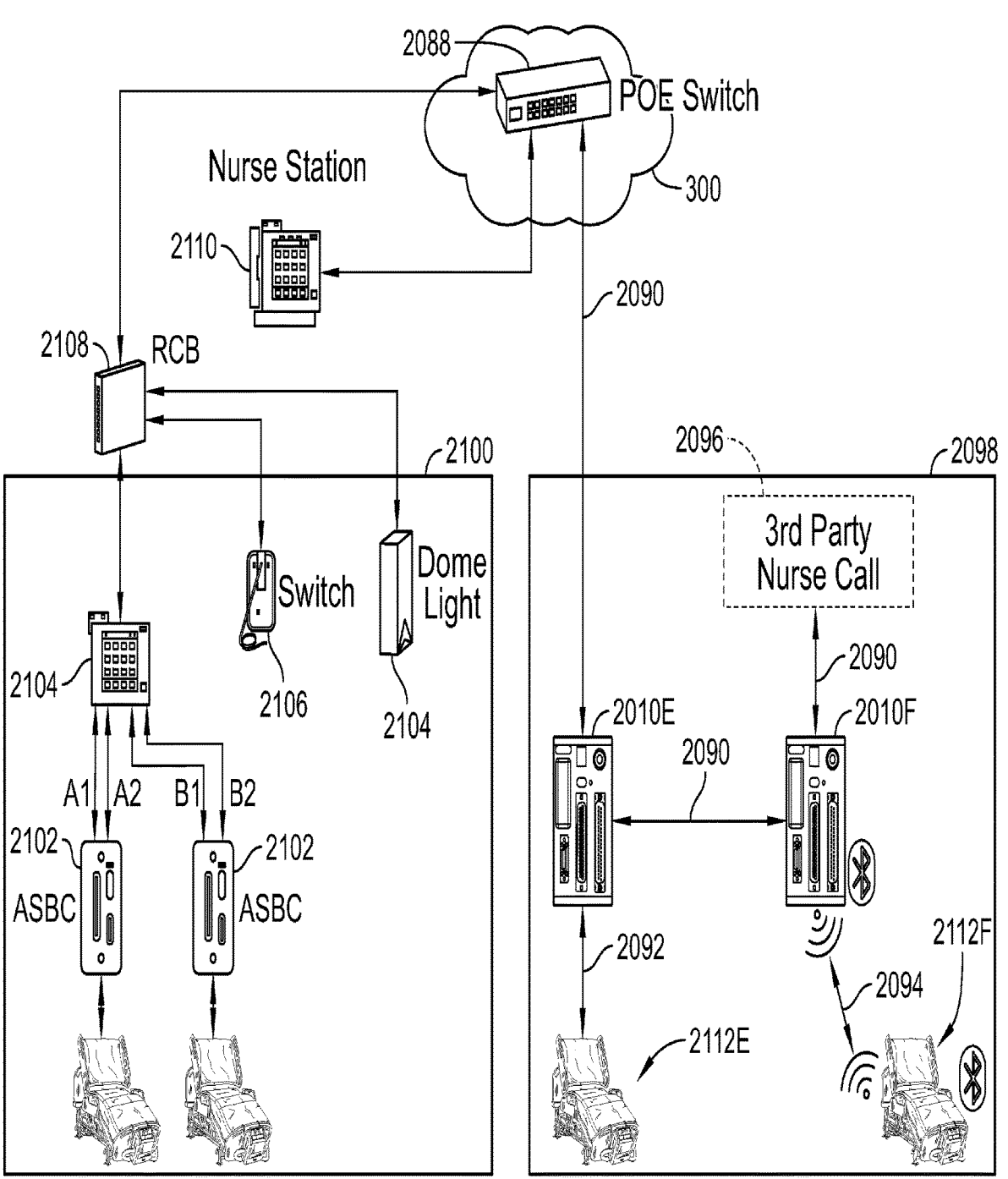
FIG. 17 is a diagrammatic arrangement of a number of communications hubs configured for use in a room of a care facility which is not equipped with a particular nurse call system, in conjunction with another room of the care facility which is equipped with the particular nurse call system.

Referring now to FIGS. 16 and 17, exemplary arrangements of communications hubs 2010 within care facilities are shown. The exemplary arrangement of FIG. 16, represents one suitable implementation of communications hubs 2010 in room(s) of a care facility, the room(s) are illustratively not equipped with a preferred nurse call system such as, for example, the Navicare® Nurse Call (NNC) system marketed by Hill-Rom Company, Inc. of Batesville, Indiana 47006. In the illustrative embodiment of FIG. 16, a number of communications hubs 2010A-D are shown in communication with respective patient beds 2112A-2112D.

The communications hub 2010A illustratively communicates with the network 300 through a power-over-Ethernet (POE) switch 2088 (shown as part of network 300, but in some embodiments, may be distinct and in communication with network 300) as shown in FIG. 16. Communications hubs 2010B-2010C are illustratively arranged in communication with the network 300 through the communications hub 2010A via links 2090, embodied as hardwiring. In the illustrative embodiment, the communications hubs 2010A, 2010B are connected to communicate with their respective beds 2112A, 2112B via hardwired bed links 2092 and the communications hubs 2010C, 2010D are illustratively connected to communicate with their respective beds 2112C, 2112D via wireless communications links 2094, such as Bluetooth LE 4.0 communications in some embodiments.

The communications hub 2010D is illustratively arranged in communication with a third party nurse call system 2096 to conduct nurse call communications. The communications hubs 2010A-2010C are illustratively arranged in communication with the third party nurse call system 2096 through communications hub 2010D. The communications hubs 2010A-2010D are illustratively located within the same room of the care facility, but in some embodiments may be located in different rooms, for example but without limitation, rooms with close proximity and/or sharing walls. Moreover, in some embodiments, each of the individual communications links 2090, 2092, 2094 may be wholly or partly wired and/or wireless links.

Referring now to the exemplary arrangement of FIG. 17, a number of communications hubs 2010E, 2010F are shown in communication with respective patient beds 2112E, 2112F via wired bed communications link 2092 and wireless communications link 2094, respectively. Similar to the arrangement of FIG. 16, the communications hubs 2010E, 2010F are located within a room 2098 that is illustratively not equipped with a preferred nurse call system. The communications hubs 2010E, 2010F are illustratively arranged in communication with each other and with the network 300 through communication links 2090. The communications hub 2010F provides communication with an optional third party nurse call system 2096 through the respective communications link 2090, but in some embodiments, the third party nurse call system 2096 may be formed as part of the network 300 or may be excluded. As will become more clear with the description below, the optional third party nurse call system 2096 may include arrangements in which different portions of the same care facility may have different legacy nurse call systems. Another room 2100 of the care facility is embodied as equipped with the preferred Navicare® Nurse Call (NNC) system.

As shown in FIG. 17, the room 2100 illustratively includes Audio Station Bed Connectors (ASBC) 2102 in communication with one or more graphical room stations (GRS) 2104 which can include graphical user interfaces for interaction with patients and/or staff and located within the room 2100. Also associated with the room 2100 is a dome light 2105 (located in a hallway near a door to room 2100) and a nurse call switch 2106 within the room 2100. Each of the ASBC, 2102, GRS 2104, dome light 2105, and nurse call switch 2106 is illustratively arranged in communication with a room control board 2108. The room control board 2108 is illustratively embodied as a dedicated device for each room equipped with the preferred nurse call system providing communication with the network 300. Another GRS 2110 is illustratively arranged at a master nurse station but such stations may be fixed and/or portable and/or located at other staff workstations for communications with the network 300, patient beds 2112, and/or other devices and systems.

In the exemplary arrangement of FIG. 17, each of the non-NNC equipped room 2098 and the NNC-equipped room 2100 communicate with the network 300 through the POE switch 2088. Accordingly, non-NNC equipped rooms and the NNC-equipped rooms of the same facility can each communicate with the hospital network 300 and with each other as needed. As suggested in FIG. 17, various room devices, including the GRS 2104 (including the ASBC's 2102 via the GRS 2104), dome lights 2105, and switches 2106, individually connect with the room control board 2108 to communicate with the network 300 and GRS 2110 with a multi-level architecture. In comparison, the communications hubs 2010 enable bed-centric communications/control/monitoring of various room devices and systems in communication with the network 300 and/or third party nurse call systems 2096, with room-localized networking.

Figure 18:
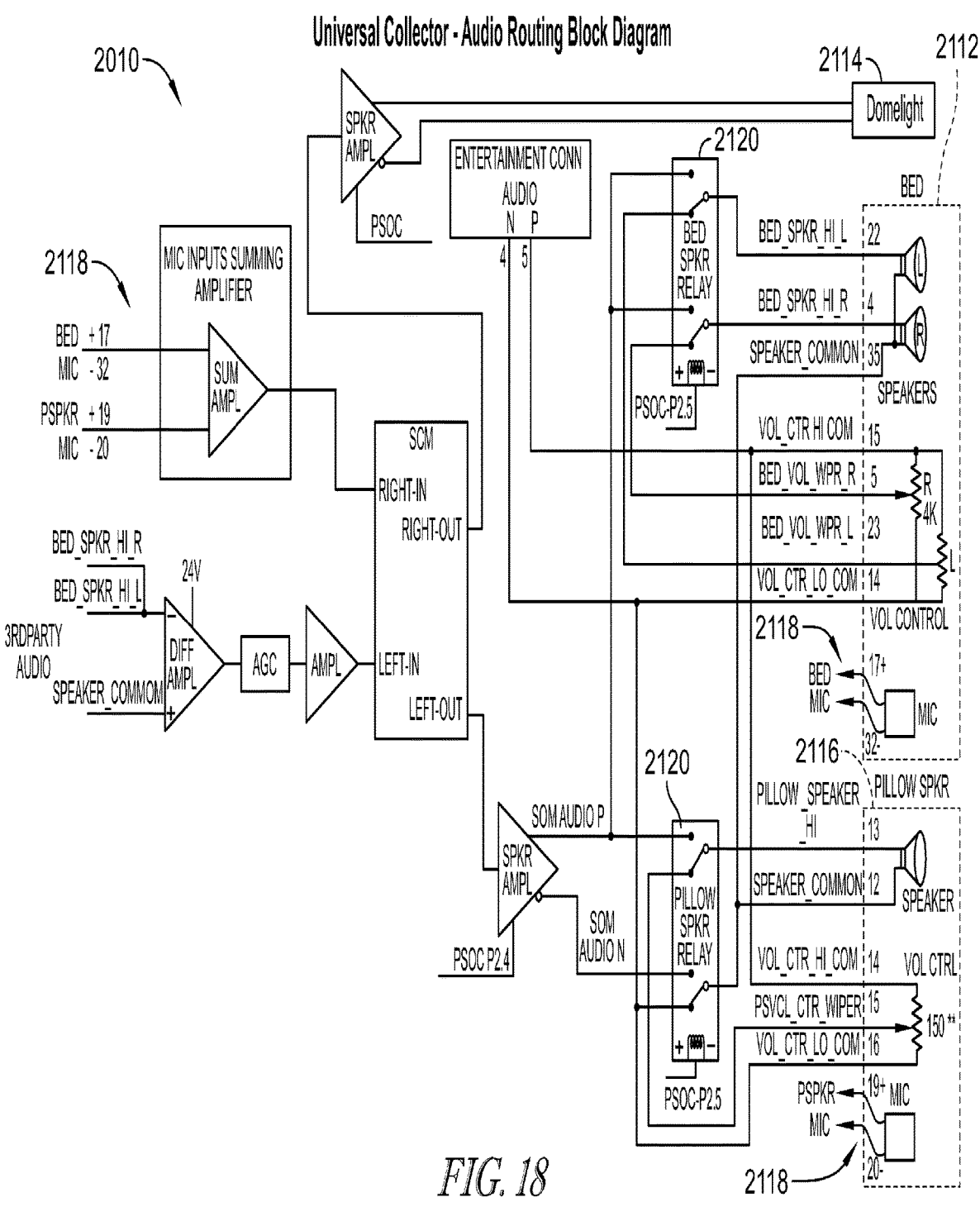
FIG. 18 is an exemplary circuit schematic of an audio routing configuration of the communications hub.

Referring now to FIG. 18, an exemplary audio routing arrangement of the communications hub 2010 is shown. Hub 2010 is labeled as "Universal Collector" in FIG. 18 to indicate the hub's ability to receive data from a variety of different patient devices. The communications hub 2010 is illustratively arranged to route audio for each of the dome light 2114, the bed 2112, and the pillow speaker 2116. The communications hub 2010 illustratively receives microphone inputs 2118 (e.g., sample line level analog signals) from each of the pillow speaker 2116 and the bed 2112 and communicates audio signals between the bed 2112, the pillow speaker 2116, and various devices (e.g., television, radio, nurse call, etc.). The communications hub 2010 illustratively includes various audio circuitry (e.g., amplifiers, gain controllers, etc.) for conditioning audio signals and speaker relays 2120 for operating each of the bed 2112 and the pillow speaker 2116 for audio communication, including in accordance with their respective volume control levels.

As may or may not be indicated within the figures, the present disclosure includes one or more communications hubs, which may be referred to as Universal Collectors, and may be adapted for use with the NNC system. In some embodiments, each communications hub can be adapted to provide power to room-level devices and systems such as room stations (e.g., standard or graphical), light stations (e.g., segmented dome light), and/or other communications hubs. The communications hubs, when connected to a patient bed via Bluetooth and/or other wireless link can be operated as an audio station bed connector, network interface unit, and/or bed sidecom. The communications hubs can be arranged to mute entertainment audio, upon and/or during communication of a preferred communication, for example, a staff and/or patient communication. The communications hubs can be arranged to communicate audio wirelessly to a patient bed, for example, by Bluetooth, from any of the devices connected with its 14-pin entertainment connector, connected room stations, and/or from its third party 37-pin nurse call connector. The communications hubs can be arranged to communicate entertainment control signals received from a patient bed to its 14-pin connector to communicate with devices such as televisions, lighting, climate control, and/or other room controls. The communications hubs can be arranged to detect connection of a patient bed with its 37 pin connector.

The present disclosure includes devices, systems, and methods for location determination, tracking, and utilization such that when an object or person with an emitter walks through a mesh of receivers, the receivers within range will query all peers whether they see that particular emitter, and if so, the signal strength; each of the peer devices repeat the previous operation until the emitter is no longer observed; eventually all receivers will have a table of signal strengths for the emitter and it peers. The receiver that has the strongest signal can then, with a relative high level of confidence, know that it is the closest receiver to the emitter.

The present disclosure includes descriptions of the use of fixed location receivers configured in a mesh topology by a discovery process. When an emitter (object) moves within the mesh of RF receivers, the system is able to automatically associate the emitter to the nearest receiver. This can be used with algorithms (e.g. signal strength weighted moving average) to improve the confidence of the emitter location. When a receiver is activated it looks for any other receivers that are within its range and connects to them either wirelessly or wired. This will form a mesh of connected receivers that are connected to each other. Using a simple grid of receivers in which each device can only see others immediately next to them determines how the mesh is to be formed.

The present disclosure includes descriptions of a room gateway for localized decision support as well as accepting information from a broader system. The Room Gateway may be embodied as a computing device that provides acquisition and manipulation of data from providers in the room. Data providers can include devices (beds, lifts, pumps, etc.) as well as any other component in the room that generates data. Devices physically connect via a device interface that can package the data into a format that can be understood by the Gateway. The device interface implements the physical (e.g. Bluetooth, WiFi, RS485) connection as well a protocol stack that can package the device data into a format that can processed by the gateway. The Gateway can be configured with multiple protocol handlers that will enable it to act on data from multiple device types.

Data received from the devices can include the following: a data point can be combined with one or more data points from other devices to help in decision support Immediate results can then be sent to other devices as an actionable event to caregivers or patients; consolidated data is also sent to a server (e.g. EMR, HIS, etc.) for further processing and analysis; device status is an event that represents the health and current operational state of the device; consolidated status is also sent to the server (e.g. EMR, HIS, etc.) for further processing and analysis; and a command message can be used to initiate interactions between two devices that have different protocols. Data received from the server can include the following: patient and caregiver information can be forwarded on to the devices to configure them for the particular needs of the patient or staff; workflow instructions to automate repetitive tasks; and events that require staff or patient attention. The Gateway may be one of several processing tiers. Each tier is able to provide functionality even if its parents are not available. If the Gateway loses communication with the server it can still service all the devices in the room as well as provide intermediate storage for processed data until the server is available again. An example of multiple tiers may include Server (Data storage and analysis, extended decision support); Room Gateway (Device data aggregation, event processing, localized decision support); Device Interface (Device communication, data packaging); and Device (Data source).

The present disclosure includes leveraging existing communications framework for real time location systems (RTLS) to exchange data between devices and to associate devices to a location and/or a patient. The communication framework may be leveraged to establish connectivity and associations between devices and locations for exchanging and gathering of data. For example, by capturing device data from a device (e.g., bed data from a bed) using a Wi-Fi connection (or other wireless connection) of a locating component (RTLS/Wi-Fi locator badge) used to associate the device (bed) with the location; and upon recognition that another patient device (e.g., a patient lift) is also discovered and associated with the same location using a locating (RTLS/Wi-Fi locator badge), the devices (e.g., lift and bed) can communicate with each other. In some embodiments, the device may communicate over the locating Wi-Fi connection to exchange data. Such arrangement may be used to raise or lower a bed for lift height to assist patient and caregiver when moving a patient and/or capture weight of patient seamlessly. Automated device association promotes interconnectivity and information sharing.

The present disclosure includes devices, systems, and methods for dynamic locating by taking into account patterns as well as historical data to determine person or object location. This allows for precise locating that adapts to changes in the environment. For example, in an arraignment having three locating receivers (nodes) equidistant from each other (and for example at 0 degrees, 120 degrees, and 240 degrees from the subject person and/or object), a staff member with a locating transmitter facing node 1 would receive a higher signal strength than other nodes. The system may record locator transmitter information as each node and combine multiple data points (beyond simple geometries) over time based off nodes within a given area (e.g., a room) to make better assessment of person and/or object location.

The present disclosure includes descriptions of location tracking including consideration of a locator tag's velocity, acceleration, rotation, positioning, and/or combinations thereof. The locator tag illustratively include various sensors that may be embodied as any of accelerometers, gyroscopes, and/or compasses, to communicate acceleration, orientation, and/or positioning data for use in determining the location of the locator tag. The system may apply dynamic weighting of the accuracy of these variables to determine location with accuracy. A locator tag may communicate the data to a receiver, which may optionally measure signal strength. The receiver communicates the data (and optionally the signal strength) to a central computing device that determines location of the locator tag based on the data (and optionally the signal strength), historical information, and/or predictive determination.

Although certain illustrative embodiments have been referenced within this disclosure, variations and modifications exist within the scope and spirit of this disclosure as described and as defined in the claims below.

The invention claimed is:

1. A patient support apparatus for use in a healthcare facility having a network with a wireless access point, a server, and at least one network device adapted to communicate with both the network and a second device remote from the patient support apparatus, the patient support apparatus comprising:

a mattress adapted to support a patient thereon;

a wireless transmitter adapted to transmit data to the server via a first path or a second path, the first path including the second device remote from the patient support apparatus but excluding the wireless access point and all other wireless access points of the network, the second path including the wireless access point but excluding the second device remote from the patient support apparatus, the first and second paths each extending all of the way from the patient support apparatus to the server; and a controller adapted to control when the wireless transmitter transmits data from the patient support apparatus to the server via the first path and when the wireless transmitter transmits data to the server via the second path, wherein the controller is further configured for communication with the server via an all-wired path that includes the second device and a cable that is coupleable to a port of the patient support apparatus.

2. The patient support apparatus of claim 1, wherein the second device comprises a gateway.

3. The patient support apparatus of claim 1, wherein the wireless transmitter comprises a first wireless transmitter and a second wireless transmitter.

4. The patient support apparatus of claim 1, wherein the wireless transmitter comprises a WiFi transmitter and a Bluetooth transmitter.

5. The patient support apparatus of claim 1, wherein the wireless transmitter is included as part of a wireless transceiver of the patient support apparatus.

6. The patient support apparatus of claim 5, further comprising an infrared transmitter or infrared receiver.

7. The patient support apparatus of claim 1, wherein the second device comprises a Power over Ethernet switch.

8. The patient support apparatus of claim 1, wherein the wireless transmitter communicates wirelessly with a wall unit fixed in place in a room in which the patient support apparatus is located.

9. The patient support apparatus of claim 8, wherein the wall unit is included in the first path.

10. The patient support apparatus of claim 8, further comprising a first connector and wherein the wall unit includes a second connector, the first and second connectors being coupleable for wired communication by the cable.

11. The patient support apparatus of claim 10, wherein the first and second connectors each comprise a 37-pin connector.

12. The patient support apparatus of claim 11, wherein the wall unit further comprises a 20-pin connector for wired connection with a pillow speaker unit.

13. The patient support apparatus of claim 12, wherein the wall unit further comprises a ¼ inch jack receiver for wired connection to a patient care device for receipt of an alarm signal from the patient care device.

14. The patient support apparatus of claim 11, wherein the wall unit further comprises an HDMI port.

15. The patient support apparatus of claim 11, wherein the wall unit includes a USB port.

16. The patient support apparatus of claim 8, wherein the wireless transmitter is configured to transmit audio signals to the wall unit.

17. The patient support apparatus of claim 1, wherein the wireless transmitter is also configured to communicate wirelessly with a tablet computer.

18. The patient support apparatus of claim 1, wherein the wireless transmitter is also configured to communicate wirelessly with a pillow speaker unit.

19. The patient support apparatus of claim 1, wherein the wireless transmitter is configured to communicate using multiple different wireless communication protocols.

20. The patient support apparatus of claim 1, wherein the wireless transmitter is configured to communication through a firewall with a server that is located outside the healthcare facility.

\*  \*  \*  \*  \*